(12) United States Patent
Lo et al.

(10) Patent No.: US 7,026,162 B2
(45) Date of Patent: Apr. 11, 2006

(54) LAC SHUTTLE VECTORS

(75) Inventors: Wei-Yu Lo, Taipei (TW); Pei-Ru Liau, Taipei (TW)

(73) Assignee: Anawrahta Biotech Co., Ltd., Taipei-Shien (TW)

( * ) Notice: Subject to any disclaimer, the term of this patent is extended or adjusted under 35 U.S.C. 154(b) by 0 days.

(21) Appl. No.: 09/778,516

(22) Filed: Feb. 7, 2001

(65) Prior Publication Data
US 2002/0102722 A1 Aug. 1, 2002

(30) Foreign Application Priority Data
May 26, 2000 (TW) ............................... 89110235 A

(51) Int. Cl.
*C12N 15/75* (2006.01)
*C12Q 1/00* (2006.01)
*C12Q 1/02* (2006.01)
*A61K 48/00* (2006.01)

(52) U.S. Cl. ........................... 435/320.1; 435/4; 435/6; 435/14; 435/7.37; 424/93.21; 514/44; 536/23.1

(58) Field of Classification Search ............. 435/320.1, 435/4, 6, 14, 7.37, 737; 424/93.21; 514/44; 536/23.1
See application file for complete search history.

(56) References Cited

OTHER PUBLICATIONS

Ertl et.al.; Genetic Immunization, 1996, Viral Immunology vol. 9, No. 1: 1-9.*
Ross et.al.; Gene Therapy in the United States: A five-Year Status Report, 1996, Human Gene Therapy 7: 1781-1790.*
Fox; No winners against AIDS, 1994, Bio/Technology vol. 12: 128.*
Yasutomi; A Vaccine-Elicited, Single Viral Epitope-specificSpecific CytotoxicTLymphocyte . . . Simian Immunodeficiency Virus Challenge, 1995, Journal of Virology: 2279-2284.*
Monteil et.al.; Genetic Immunization of seronegative one-day-old piglets against pseudorabies induces neutralizing antibodies but not protection and is ineffective in piglets from Immune dams, 1996, Elsevier 27: 443-452.*
Orkins et.al.; Report and Recommendations of the Panel to Assess the NIH Investment in Research on Gene Therapy, 1995.*
Bringel et.al.; Characterization, Cloning, Curing, and Distribution in Lactic Acid Bacteria of pLP1, a Plasmid . . . Its use in Shuttle Vector Construction, 1989, Plasmid 22: 193-202.*

Hemme et.al.; Expression of *Lactobacillus casei* ATCC 393 . . . in *Lactococcus lactis* CNRZ . . . 1123, 1994, Letters in Applied Microbiology 19: 345-348.*
Dietrich et.al; Delivery of antigen-encoding plasmid DNA into the cytosol of macrophages by attenuated suicide *Listeria monocytogenes*, 1998, Nature Biotechnology, vol. 18: 181-185.*
de Vos W.M. Safe and sustainable systems for food-grade fermentations by genetically modified lactic acid bacteria. International Dairy Journal, (1999) vol. 9, No. 1, pp. 3-10.*
Cocconcelli et al. Genetic analysis of the replication region of the *Lactobacillus* plasmid□□pPSC22. Res Microbiol. Oct. 1996;147(8):619-24.*
Kanatani et al. Identification of the replication region of *Lactobacillus acidphilus* plasmid□□pLA103. FEMS Microbiol Lett. Nov. 1,1995;133(1-2):127-30.*
Klein et al. Characterization and sequence analysis of a small cryptic plasmid from□□*Lactobacillus curvatus* LTH683 and its use for construction of new *Lactobacillus*□□cloning vectors. Plasmid. Jul. 1993;30(1): 14-29.*
Imanaka et al. Complete nucleotide sequence of the low copy number plasmid pRAT11 and □□replication control by the RepA protein in *Bacillus subtilis*. Mol Gen Genet. Oct. 1986;205(1):90-6.*
Sorensen et al. A food-grade cloning system for industrial strains of *Lactococcus lactis*.□□Appl Environ Microbiol. Apr. 2000;66(4):1253-8.*
Platteeuw et al. Food-grade cloning and expression system for *Lactococcus lactis*.□□Appl Environ Microbiol. Mar. 1996;62(3):1008-13.*
Bouia et al. Structural organization of pLP1, a cryptic plasmid from *Lactobacillus planatarum* CCM 1904. Plasmid. Nov. 1989;22(3):185-92.*

* cited by examiner

*Primary Examiner*—David Guzo
*Assistant Examiner*—Daniel M. Sullivan
(74) *Attorney, Agent, or Firm*—Fish & Richardson P.C.

(57) ABSTRACT

The invention discloses a Lac shuttle vector, comprising at least (a) a region which regulates a plasmid copy number; (b) an eukaryotic gene expression cassette, which comprises at least an eukaryotic gene transcriptional promoter sequence, a multiple cloning site and a transcriptional terminator sequence; (c) a lactic acid bacteria plasmid sequence, which comprises a plus origin of replication, and a nucleic acid sequence encoding for a protein which relates to the lactic acid bacteria plasmid replication; and (d) a non-antibiotic resistance selection gene and the promoter sequence thereof. The Lac shuttle vector features a non-antibiotic resistance gene as a selection marker, which is useful in pharmaceuticals and foods.

14 Claims, 19 Drawing Sheets

```
         10         20         30         40         50         60
GATGTACGGG CCAGATATAC GCGTTGACAT TGATTATTGA CTAGTTATTA ATAGTAATCA 70         80         90        100        110        120
ATTACGGGGT CATTAGTTCA TAGCCCATAT ATGGAGTTCC GCGTTACATA ACTTACGGTA 130        140        150        160        170        180
AATGGCCCGC CTGGCTGACC GCCCAACGAC CCCCGCCCAT TGACGTCAAT AATGACGTAT 190        200        210        220        230        240
GTTCCCATAG TAACGCCAAT AGGGACTTTC CATTGACGTC AATGGGTGGA CTATTTACGG 250        260        270        280        290        300
TAAACTGCCC ACTTGGCAGT ACATCAAGTG TATCATATGC CAAGTACGCC CCCTATTGAC 310        320        330        340        350        360
GTCAATGACG GTAAATGGCC CGCCTGGCAT TATGCCCAGT ACATGACCTT ATGGGACTTT 370        380        390        400        410        420
CCTACTTGGC AGTACATCTA CGTATTAGTC ATCGCTATTA CCATGGTGAT GCGGTTTTGG 430        440        450        460        470        480
CAGTACATCA ATGGGCGTGG ATAGCGGTTT GACTCACGGG GATTTCCAAG TCTCCACCCC 490        500        510        520        530        540
ATTGACGTCA ATGGGAGTTT GTTTTGGCAC CAAAATCAAC GGGACTTTCC AAAATGTCGT 550        560        570        580        590        600
AACAACTCCG CCCCATTGAC GCAAATGGGC GGTAGGCGTG TACGGTGGGA GGTCTATATA 610        620        630        640        650        660
AGCAGAGCTC TCTGGCTAAC TAGAGAACCC ACTGCTTACT GGCTTATCGA AATTAATACG 670        680        690        700        710        720
ACTCACTATA GGGAGACCCA AGCTTGGTAC CGAGCTCGGA TCCACTAGTA ACGGCCGCCA 730        740        750        760        770        780
GTGTGCTGGA ATTCTGCAGA TATCCATCAC ACTGGCGGCC GCTCGAGCAT GCATCTAGAG 790        800        810        820        830        840
GGCCCTATTC TATAGTGTCA CCTAAATGCT AGAGCTCGCT GATCAGCCTC GACTGTGCCT 850        860        870        880        890        900
TCTAGTTGCC AGCCATCTGT TGTTTGCCCC TCCCCCGTGC CTTCCTTGAC CCTGGAAGGT 910        920        930        940        950        960
GCCACTCCCA CTGTCCTTTC CTAATAAAAT GAGGAAATTG CATCGCATTG TCTGAGTAGG 970        980        990       1000       1010       1020
TGTCATTCTA TTCTGGGGGG TGGGGTGGGG CAGGACAGCA AGGGGGAGGA TTGGGAAGAC 1030       1040       1050       1060       1070       1080
AATAGCAGGC ATGCTGGGGA TGCGGTGGGC TCTATGGCTT CTGAGGCGGA AAGAACCAGC 1090       1100       1110       1120       1130       1140
TGCATTAATG AATCGGCCAA CGCGCGGGGA GAGGCGGTTT GCGTATTGGG CGCTCTTCCG 1150       1160       1170       1180       1190       1200
CTTCCTCGCT CACTGACTCG CTGCGCTCGG TCGTTCGGCT GCGGCGAGCG GTATCAGCTC
```

FIG. 5A

```
     1210       1220       1230       1240       1250       1260
ACTCAAAGGC GGTAATACGG TTATCCACAG AATCAGGGGA TAACGCAGGA AAGAACATGT 1270       1280       1290       1300       1310       1320
GAGCAAAAGG CCAGCAAAAG GCCAGGAACC GTAAAAAGGC CGCGTTGCTG GCGTTTTTCC 1330       1340       1350       1360       1370       1380
ATAGGCTCCG CCCCCCTGAC GAGCATCACA AAAATCGACG CTCAAGTCAG AGGTGGCGAA 1390       1400       1410       1420       1430       1440
ACCCGACAGG ACTATAAAGA TACCAGGCGT TTCCCCCTGG AAGCTCCCTC GTGCGCTCTC 1450       1460       1470       1480       1490       1500
CTGTTCCGAC CCTGCCGCTT ACCGGATACC TGTCCGCCTT TCTCCCTTCG GGAAGCGTGG 1510       1520       1530       1540       1550       1560
CGCTTTCTCA ATGCTCACGC TGTAGGTATC TCAGTTCGGT GTAGGTCGTT CGCTCCAAGC 1570       1580       1590       1600       1610       1620
TGGGCTGTGT GCACGAACCC CCCGTTCAGC CCGACCGCTG CGCCTTATCC GGTAACTATC 1630       1640       1650       1660       1670       1680
GTCTTGAGTC CAACCCGGTA AGACACGACT TATCGCCACT GGCAGCAGCC ACTGGTAACA 1690       1700       1710       1720       1730       1740
GGATTAGCAG AGCGAGGTAT GTAGGCGGTG CTACAGAGTT CTTGAAGTGG TGGCCTAACT 1750       1760       1770       1780       1790       1800
ACGGCTACAC TAGAAGGACA GTATTTGGTA TCTGCGCTCT GCTGAAGCCA GTTACCTTCG 1810       1820       1830       1840       1850       1860
GAAAAAGAGT TGGTAGCTCT TGATCCGGCA AACAAACCAC CGCTGGTAGC GGTGGTTTTT 1870       1880       1890       1900       1910       1920
TTGTTTGCAA GCAGCAGATT ACGCGCAGAA AAAAAGGATC TCAAGAAGAT CCTTTGATCT 1930       1940       1950       1960       1970       1980
TTTCTACGGG GTCTGACGCT CAGTGGAACG AAAACTCACG TTAAGGGATT TTGGTCATGA 1990       2000       2010       2020       2030       2040
GCGGATACAT ATTTGAATGT ATTTAGAAAA ATAAACAAAT AGGGGTTCCG CGCACATTTC 2050       2060       2070       2080       2090       2100
CCCGAAAAGT GCCACCTGAC GTCGACGGAT CGGGAGATCA ACGGTAAATC CGTTGGCATA 2110       2120       2130       2140       2150       2160
TCCCTTTTTT GTTGTCAGCT TGCTGACTTC TGATACAGGT TTTAGCATTA CTCCAATTTA 2170       2180       2190       2200       2210       2220
TTTGGAGTGT AAGTGCACAT TATCATGTAG TGCGCATTAT CATGTAGTGC GCATTATCAT 2230       2240       2250       2260       2270       2280
GTAGTGCGCA TTATCATGTA GTGCGCATTA TCATGTAGTG CGCATTATCA TGTAGTGCGC 2290       2300       2310       2320       2330       2340
ATTATCATGT AGTGCGCACA TTATCATGTA CATTATCATG TAGTGCGCAT TATCATGTAG 2350       2360       2370       2380       2390       2400
TGCGCACATT ATCATGTAGT GCGCATTATC ATGTAGTGCG CATTATCATG TAGTGCGCAC
```

FIG. 5B

```
       2410       2420       2430       2440       2450       2460
  TTACACACAA CATGAAGTTG TGTTGTGCTA AACCCATCAA AACCTGCATC AGATTTCGCG 2470       2480       2490       2500       2510       2520
  TTGCTCAAAC GTAACTGACT TGCGTCAGTT TGGAACATTC AAAAATAAAT AAGTTCAGTC 2530       2540       2550       2560       2570       2580
  GCTAGCTCCT TCGAACTTTT TTATTTTTGA ACGTTAATTT TAAAGGCTCT TATTTGCGTT 2590       2600       2610       2620       2630       2640
  CTAAGCGATT TTAGCTAACA GTTAGCTATC TAACTGTCTG TCAACGGTAA ATCGACTTAG 2650       2660       2670       2680       2690       2700
  AGGGGCTTAT TGAGCCTTAC AGGCGATATT AGCCCCTCTT GGAGGCTTTA AGGAGTTGAT 2710       2720       2730       2740       2750       2760
  AGACTAGACA ATACCAAAAG CCTGACGTCT TGGAAAACAA GCCCTTGTTT TCCCGAGCCC 2770       2780       2790       2800       2810       2820
  AGCGGCGGCA AGCGTTACGG TCCAGCTGGT TCAGCTGGTC AGTGTGGCTG AAAGCCACGG 2830       2840       2850       2860       2870       2880
  TTTAAAAAAA GCAGTTCAGC GGTTTTTGCT GATCTGCTTT TTGGGGTTTA AAAACGCAAT 2890       2900       2910       2920       2930       2940
  TTTTGGCGTT TTCTTCTTAT CTTGATACTA TTAGCAACAA CTAGTTTTTT AAAATCAAGC 2950       2960       2970       2980       2990       3000
  TTGATTAGGC TTAATTGGGC TTGTATCCAT TGATTTTATA GGCTTTTGGT GTATTATTAG 3010       3020       3030       3040       3050       3060
  GGTTATAAAT TGGTTGAAAG AAAGACAAAA TAAAAACCCA CGTGCAAATT CCTAGTTTGG 3070       3080       3090       3100       3110       3120
  CCGCTCGGAA CACGTGAGTT GATTATCATT TGCGATTTAT AGCCTATTCT AGGGGAAAAG 3130       3140       3150       3160       3170       3180
  CCCTATGATG TCAAGGTTAT AAGCTTATTG AAAAAGATAG TCAGCTCCTT CACGTGGATA 3190       3200       3210       3220       3230       3240
  AACTGGAGGA GCTTTTTATG TCAGAAATTT TTGAAGATAA AACTGAAAAT GGCAAAGTTA 3250       3260       3270       3280       3290       3300
  GACCTTGGCG AGAACGGAAG ATTGAAAATG TGCGCTATGC CGAATATTTG GCAATCTTAG 3310       3320       3330       3340       3350       3360
  AATTTAAACG GGCACATGAT GTACGGGGTT GTGGTGAAGT TTTGCGTTTT CGTAAGATTG 3370       3380       3390       3400       3410       3420
  GCGAGCACTT AAAACTTTAT CAAACGTGGT TTTGTCATAA ACGATTGTGT CCATTGTGTA 3430       3440       3450       3460       3470       3480
  ATTGGAGAAG GAGCATGAAA AACTCGAGCC AGTTAAAACA AATTATTGCG GAAGCAGTTG 3490       3500       3510       3520       3530       3540
  CAAGAGAGCC TAAAGGACGG TTTTTGTTTT TAACTTTAAC CGTTAAAAAC GCTCATTCAG 3550       3560       3570       3580       3590       3600
  CAGAGGAGTT AAAAGTGTCT TTAAGAGCTT TGACTAAAGC CTTTAATAAG CTAACTCGCT
```

FIG. 5C

```
      3610       3620       3630       3640       3650       3660
ATAAAAAAGT GACTAAAAAT TTATTGGGTT ATTTACGTTC AACGGAAATT ACCGTTAATG 3670       3680       3690       3700       3710       3720
AACAAGACGG GTCATATAAT CAACACTTGC ATGTGTTGCT GTTTGTAAAA TCAAGTTATT 3730       3740       3750       3760       3770       3780
TTAAGAATTC AAATAATTAT TTAGCACAAG CAGAATGGGC AAAATTATGG CAAAAAGCCT 3790       3800       3810       3820       3830       3840
TGAAAGTTGA TTATGAGCCT GTGGTGCATG TGCAGGCTGT TAAAGCTAAC AAACGTAAAG 3850       3860       3870       3880       3890       3900
GAACTGACTC TTTGCAAGCT AGTGCCGAAG AAACGGCGAA ATACGAGGTA AAATCAGCTG 3910       3920       3930       3940       3950       3960
ATTATATGAC GGCTGATGAT GAGCGTAATT TGGTGGTGAT TAAAAATTTG GAGTATGCCT 3970       3980       3990       4000       4010       4020
TAGCTGGAAC ACGACAAATC AGCTATGGTG GATTATTAAA GCAAATTAAG CAAGATTTGA 4030       4040       4050       4060       4070       4080
AACTTGAAGA TGTTGAGAAT GGTGATTTAG TTCATGTTGG CGATGAAGAT TACACCAAAG 4090       4100       4110       4120       4130       4140
AGCAAATGGA AGCTGCGGAA GAAGTTGTCG CAAAATGGGA TTTTAATAAA CAAAATTATT 4150       4160       4170       4180       4190       4200
TTATTTGGTA AAGAGAATGT CAGGATATGA TCTCCCGATC CCCTATGGTC GACTCTCAGT 4210       4220       4230       4240       4250       4260
ACAATCTGCT CTGATGCCGC ATAGTTAAGC CAGTATCTGC TCCCTGCTTG TGTGTTGGAG 4270       4280       4290       4300       4310       4320
GTCGCTGAGT AGTGCGCGAG CAAAATTTAA GCTACAACAA GGCAAGGCTT GACCGACAAT 4330       4340       4350       4360       4370       4380
TGCATGAAGA ATCTGCTTAG GGTTAGGCGT TTTGCGCTGC TTCGTTAGAA GCAAACTAAG 4390       4400       4410       4420       4430       4440
AGTGTGTTGA GTAGTGCAGT ATCTTAAAAT TTTGTATAAT AGGAATTGAA GTTAAATTAG 4450       4460       4470       4480       4490       4500
ATGCTAAAAA TTTGTAATTA AGAAGGAGTG ATTACATGAT TGGCAGCCAG TCTCCGGGCA 4510       4520       4530       4540       4550       4560
ATTAATGAAC TTGGACATGG TTGACGACCC GGTCTTTGCA AGCCGAATTC GACCACACTG 4570       4580       4590       4600       4610       4620
GCGGCCGTTA CTAGGGTATC GATCCGATAA AAAGTTAGGC GACGGCTTTG CCCTGGTGCC 4630       4640       4650       4660       4670       4680
AGCAGACGGT AAGGTCTACG CGCCATTTGC CGGTACTGTC CGCCAGCTGG CCAAGACCCG 4690       4700       4710       4720       4730       4740
GCACTCGATC GTCCTGGAAA ATGAACATGG GGTCTTGGTC TTGATTCACC TTGGCCTGGG 4750       4760       4770       4780       4790       4800
CACGGTCAAA TTAAACGGGA CTGGCTTTGT CAGCTATGTT GAAGAGGGCA GCCAGGTAGA
```

FIG. 5D

```
       4810       4820       4830       4840       4850       4860
  AGCCGGCCAG CAGATCCTGG AATTCTGGGA CCCGGCGATC AAGCAGGCCA AGCTGGACGA 4870       4880       4890       4900       4910       4920
  CACGGTAATC GTGACCGTCA TCAACAGCGA AACTTTCACA AATAGCCAGA TGCTCTTGCC 4930       4940       4950       4960       4970       4980
  GATCGGCCAC AGCGTCCAAG CCCTGGATGA TGTATTCAAG TTAGAAGGGA AGAATTAGAA 4990       5000       5010       5020       5030       5040
  AATGAGCAAT AAGTTAGTAA AAGAAAAAAG AGTTGACCAG GCAGACCTGG CCTGGCTGAC 5050       5060       5070       5080       5090       5100
  TGACCCGGAA GTTTACGAAG TCAATACAAT TCCCCCGCAC TCCGACCATG AGTCCTTCCA 5110       5120       5130       5140       5150       5160
  AAGCCAGGAA GAACTGGAGG AGGGCAAGTC CAGTTTAGTG CAGTCCCTGG ACGGGACTG 5170       5180       5190       5200       5210       5220
  GCTGATTGAC TACGCTGAAA ACGGCCAGG ACCAGTCAAC TTCTATGCAG AAGACTTTGA 5230       5240       5250       5260       5270       5280
  CGATAGCAAT TTTAAGTCAG TCAAAGTACC CGGCAACCTG GAACTGCAAG GCTTTGGCCA 5290       5300       5310       5320       5330       5340
  GCCCCAGTAT GTCAACGTCC AATATCCATG GGACGGCAGT GAGGAGATTT TCCCGCCCCA 5350       5360       5370       5380       5390       5400
  AATTCCAAGC AAAAATCCGC TCGCTTCTTA TGTCAGATAC TTTGACCTGG ATGAAGCTTT 5410       5420       5430       5440       5450       5460
  CTGGGACAAG GAAGTCAGCT TGAAGTTTGA CGGGGCGGCA ACAGCCATCT ATGTCTGGCT 5470       5480       5490       5500       5510       5520
  GAACGGCCAC TTCGTCGGCT ACGGGGAAGA CTCCTTTACC CCAAGCGAGT TTATGGTTAC 5530       5540       5550       5560       5570       5580
  CAAGTTCCTC AAGAAAGAAA ATAACCGCCT GGCAGTGGCT CTCTACAAGT ATTCTTCCGC 5590       5600       5610       5620       5630       5640
  CTCCTGGCTG GAAGACCAGG ACTTCTGGCG CATGTCTGGT TTGTTCAGAT CAGTGACTCT 5650       5660       5670       5680       5690       5700
  TCAGGCCAAG CCGCGTCTGC ACTTGGAGGA CCTTAAGCTT ACGGCCAGCT TGACCGATAA 5710       5720       5730       5740       5750       5760
  CTACCAAAAA GGAAAGCTGG AAGTCGAAGC CAATATTGCC TACCGCTTGC CAAATGCCAG 5770       5780       5790       5800       5810       5820
  CTTTAAGCTG GAAGTGCGGG ATAGTGAAGG TGACTTGGTT GCTGAAAAGC TGGGCCCAAT 5830       5840       5850       5860       5870       5880
  CAGAAGCGAG CAGCTGGAAT TCACTCTGGC TGATTTGCCA GTAGCTGCCT GGAGCGCGGA 5890       5900       5910       5920       5930       5940
  AAAGCCTAAC CTTTACCAGG TCCGCCTGTA TTTATACCAG GCAGGCAGCC TCTTAGAGGT 5950       5960       5970       5980       5990       6000
  TAGCCGGCAG GAAGTGGGTT TCCGCAACTT TGAACTAAAA GACGGGATTA TGTACCTTAA
```

FIG. 5E

```
      6010       6020       6030       6040       6050       6060
CGGCCAGCGG ATCGTCTTCA AGGGGGCCAA CCGGCACGAA TTTGACAGTA AGTTGGGTCG 6070       6080       6090       6100       6110       6120
GGCTATCACG GAAGAGGATA TGATCTGGGA CATCAAGACC ATGAAGCGAA GCAACATCAA 6130       6140       6150       6160       6170       6180
TGCTGTCCGC TGCTCTCACT ACCCGAACCA GTCCCTCTTT TACCGGCTCT GTGACAAGTA 6190       6200       6210       6220       6230       6240
CGGCCTTTAC GTCATTGATG AAGCTAACCT GGAAAGCCAC GGCACCTGGG AAAAAGTGGG 6250       6260       6270       6280       6290       6300
GGGCACGAA GATCCTAGCT TCAATGTTCC AGGCGATGAC CAGCATTGGC TGGGAGCCAG 6310       6320       6330       6340       6350       6360
CTTATCCCGG GTGAAGAACA TGATGGCTCG GGACAAGAAC CATGCTTCAA TCCTAATCTG 6370       6380       6390       6400       6410       6420
GTCTTTAGGC AATGAGTCTT ACGCCGGCAC TGTCTTTGCC CAAATGGCTG ATTACGTCCG 6430       6440       6450       6460       6470       6480
GAAGGCTGAT CCGACCCGGG TTCAGCACTA TGAAGGGGTG ACCCACAACC GGAAGTTTGA 6490       6500       6510       6520       6530       6540
CGACGCCACC CAGATTGAAA GCCGGATGTA TGCTCCGGCC AAGGTAATTG AAGAATACTT 6550       6560       6570       6580       6590       6600
GACCAATAAA CCAGCCAAGC CATTTATCTC AGTTGAATAC GCTCACGCCA TGGGCAACTC 6610       6620       6630       6640       6650       6660
CGTCGGTGAC CTGGCCGCCT ACACGGCCCT GGAAAAATAC CCCCACTACC AGGGCGGCTT 6670       6680       6690       6700       6710       6720
CATCTGGGAC TGGATTGACC AAGGACTGGA AAAAGACGGG CACCTGCTTT ATGGGGGCGA 6730       6740       6750       6760       6770       6780
CTTCGATGAC CGGCCAACCG ACTATGAATT CTGCGGGAAC GGCCTGGTCT TTGCTGACCG 6790       6800       6810       6820       6830       6840
GACTGAATCG CCGAAACTGG CTAATGTCAA GGCCCTTTAC GCCAACCTTA AGTTAGAAGT 6850       6860       6870       6880       6890       6900
AAAAGATGGG CAGCTCTTCC TCAAAAACGA CAATTTATTT ACCAACAGCT CATCTTACTA 6910       6920       6930       6940       6950       6960
CTTCTTGACT AGTCTTTTGG TCGATGGCAA GTTGACCTAC CAGAGCCGGC CTCTGACCTT 6970       6980       6990       7000       7010       7020
TGGCCTGGAG CCTGGCGAAT CCGGGACCTT TGCCCTGCCT TGGCCGGAAG TCGCTGATGA 7030       7040       7050       7060       7070       7080
AAAAGGGGAG GTCGTCTACC GGGTAACGGC CCACTTAAAA GAAGACTTGC CTTGGGCGGA 7090       7100       7110       7120       7130       7140
TGAGGGCTTC ACTGTGGCTG AAGCAGAAGA AGTAGCTCAA AAGCTGCCGG AATTTAAGCC 7150       7160       7170       7180       7190       7200
GGAAGGGCGG CCAGATTTAG TTGATTCCGA CTACAACCTA GGCCTGAAAG GAAATAACTT
```

FIG. 5F

```
          7210       7220       7230       7240       7250       7260
     CCAAATTCTC TTCTCCAAGG TCAAGGGCTG GCCGGTTTCC CTCAAGTATG CCGGTAGGGA 7270       7280       7290       7300       7310       7320
     ATACTTGAAG CGGCTGCCGG AATTTACCTT CTGGCGGGCC CTGACGGACA ACGACCGGGG 7330       7340       7350       7360       7370       7380
     AGCTGGTTAC GGCTATGATC TGGCCCGGTG GGAAAATGCC GGCAAGTATG CCCGCTTGAA 7390       7400       7410       7420       7430       7440
     AGACATCAGC TGCGAGGTCA AGGAAGACTC CGTTTTGGTC AAGACTGCCT TTACGTTGCC 7450       7460       7470       7480       7490       7500
     TGTCGCCTTA AAGGGTGATT TAACCGTGAC CTATGAAGTC GATGGACGGG GCAAGATTGC 7510       7520       7530       7540       7550       7560
     TGTAACAGCT GACTTCCCAG GCGCGGAAGA AGCTGGTCTC TTGCCAGCCT TTGGCTTGAA 7570       7580       7590       7600       7610       7620
     CCTGGCCCTG CCAAAAGAAC TGACCGATTA CCGCTACTAT GGTCTGGGAC CTAATGAGAG 7630       7640       7650       7660       7670       7680
     CTACCCAGAC CGCTTGGAAG GTAATTACCT GGGCATCTAC CAGGGAGCGG TAAAAAAGAA 7690       7700       7710       7720       7730       7740
     CTTTAGCCCA TATCGTCCGC AGGAAACGGG CAACCGGAGC AAGGTTCGCT GGTACCAGCT 7750       7760       7770       7780       7790       7800
     CTTTGATGAA AAGGGCGGCT TGGAATTTAC GGCCAATGGG GCAGACTTGA ACTTGTCTGC 7810       7820       7830       7840       7850       7860
     TTTGCCATAT TCTGCCGCCC AAAATTGAAGC AGCGGACCAC GCTTTTGAAC TGACTAACAA 7870       7880       7890       7900       7910       7920
     TTACACTTGG GTTAGAGCCT TAAGCGCCCA GATGGGGGTC GGCGGGGATG ACTCCTGGGG 7930       7940       7950       7960       7970       7980
     GCAGAAGGTC CACCCGGAAT TCTGCCTGGA TGCTCAAAAA GCCCGCCAGC TTCGCCTGGT 7990       8000       8010       8020       8030       8040
     GATTCAGCCC CTTTTACTAA AATAAATGCT ACAATTGACT TAACAGGATG AAATTTTAGT 8050       8060       8070       8080       8090       8100
     AAAAGCAAAG CGAGTGAGGA AGATGGCAAC GATCAGAGAA GTGCCAAGGC AGCCGGCGTG 8110       8120       8130       8140       8150       8160
     TCGCTAGCGA CGGTC.....  .........  .........  .........  .........
```

FIG. 5G

```
       10         20         30         40         50         60
GATGTACGGG CCAGATATAC GCGTTGACAT TGATTATTGA CTAGTTATTA ATAGTAATCA 70         80         90        100        110        120
ATTACGGGGT CATTAGTTCA TAGCCCATAT ATGGAGTTCC GCGTTACATA ACTTACGGTA 130        140        150        160        170        180
AATGGCCCGC CTGGCTGACC GCCCAACGAC CCCCGCCCAT TGACGTCAAT AATGACGTAT 190        200        210        220        230        240
GTTCCCATAG TAACGCCAAT AGGGACTTTC CATTGACGTC AATGGGTGGA CTATTTACGG 250        260        270        280        290        300
TAAACTGCCC ACTTGGCAGT ACATCAAGTG TATCATATGC CAAGTACGCC CCCTATTGAC 310        320        330        340        350        360
GTCAATGACG GTAAATGGCC CGCCTGGCAT TATGCCCAGT ACATGACCTT ATGGACTTT 370        380        390        400        410        420
CCTACTTGGC AGTACATCTA CGTATTAGTC ATCGCTATTA CCATGGTGAT GCGGTTTTGG 430        440        450        460        470        480
CAGTACATCA ATGGGCGTGG ATAGCGGTTT GACTCACGGG GATTTCCAAG TCTCCACCCC 490        500        510        520        530        540
ATTGACGTCA ATGGGAGTTT GTTTTGGCAC CAAAATCAAC GGGACTTTCC AAAATGTCGT 550        560        570        580        590        600
AACAACTCCG CCCCATTGAC GCAAATGGGC GGTAGGCGTG TACGGTGGGA GGTCTATATA 610        620        630        640        650        660
AGCAGAGCTC TCTGGCTAAC TAGAGAACCC ACTGCTTACT GGCTTATCGA AATTAATACG 670        680        690        700        710        720
ACTCACTATA GGGAGACCCA AGCTTGGTAC CGAGCTCGGA TCCACTAGTA ACGGCCGCCA 730        740        750        760        770        780
GTGTGCTGGA ATTCTGCAGA TATCCATCAC ACTGGCGGCC GCTCGAGCAT GCATCTAGAG 790        800        810        820        830        840
GGCCCTATTC TATAGTGTCA CCTAAATGCT AGAGCTCGCT GATCAGCCTC GACTGTGCCT 850        860        870        880        890        900
TCTAGTTGCC AGCCATCTGT TGTTTGCCCC TCCCCCGTGC CTTCCTTGAC CCTGGAAGGT 910        920        930        940        950        960
GCCACTCCCA CTGTCCTTTC CTAATAAAAT GAGGAAATTG CATCGCATTG TCTGAGTAGG 970        980        990       1000       1010       1020
TGTCATTCTA TTCTGGGGGG TGGGGTGGGG CAGGACAGCA AGGGGGAGGA TTGGGAAGAC 1030       1040       1050       1060       1070       1080
AATAGCAGGC ATGCTGGGGA TGCGGTGGGC TCTATGGCTT CTGAGGCGGA AAGAACCAGC 1090       1100       1110       1120       1130       1140
TGCATTAATG AATCGGCCAA CGCGCGGGGA GAGGCGGTTT GCGTATTGGG CGCTCTTCCG 1150       1160       1170       1180       1190       1200
CTTCCTCGCT CACTGACTCG CTGCGCTCGG TCGTTCGGCT GCGGCGAGCG GTATCAGCTC
```

FIG. 6A

```
      1210       1220       1230       1240       1250       1260
ACTCAAAGGC GGTAATACGG TTATCCACAG AATCAGGGGA TAACGCAGGA AAGAACATGT 1270       1280       1290       1300       1310       1320
GAGCAAAAGG CCAGCAAAAG GCCAGGAACC GTAAAAAGGC CGCGTTGCTG GCGTTTTTCC 1330       1340       1350       1360       1370       1380
ATAGGCTCCG CCCCCCTGAC GAGCATCACA AAAATCGACG CTCAAGTCAG AGGTGGCGAA 1390       1400       1410       1420       1430       1440
ACCCGACAGG ACTATAAAGA TACCAGGCGT TTCCCCCTGG AAGCTCCCTC GTGCGCTCTC 1450       1460       1470       1480       1490       1500
CTGTTCCGAC CCTGCCGCTT ACCGGATACC TGTCCGCCTT TCTCCCTTCG GGAAGCGTGG 1510       1520       1530       1540       1550       1560
CGCTTTCTCA ATGCTCACGC TGTAGGTATC TCAGTTCGGT GTAGGTCGTT CGCTCCAAGC 1570       1580       1590       1600       1610       1620
TGGGCTGTGT GCACGAACCC CCCGTTCAGC CCGACCGCTG CGCCTTATCC GGTAACTATC 1630       1640       1650       1660       1670       1680
GTCTTGAGTC CAACCCGGTA AGACACGACT TATCGCCACT GGCAGCAGCC ACTGGTAACA 1690       1700       1710       1720       1730       1740
GGATTAGCAG AGCGAGGTAT GTAGGCGGTG CTACAGAGTT CTTGAAGTGG TGGCCTAACT 1750       1760       1770       1780       1790       1800
ACGGCTACAC TAGAAGGACA GTATTTGGTA TCTGCGCTCT GCTGAAGCCA GTTACCTTCG 1810       1820       1830       1840       1850       1860
GAAAAAGAGT TGGTAGCTCT TGATCCGGCA AACAAACCAC CGCTGGTAGC GGTGGTTTTT 1870       1880       1890       1900       1910       1920
TTGTTTGCAA GCAGCAGATT ACGCGCAGAA AAAAAGGATC TCAAGAAGAT CCTTTGATCT 1930       1940       1950       1960       1970       1980
TTTCTACGGG GTCTGACGCT CAGTGGAACG AAAACTCACG TTAAGGGATT TTGGTCATGA 1990       2000       2010       2020       2030       2040
GCGGATACAT ATTTGAATGT ATTTAGAAAA ATAAACAAAT AGGGGTTCCG CGCACATTTC 2050       2060       2070       2080       2090       2100
CCCGAAAAGT GCCACCTGAC GTCGACGGAT CGGGAGATCA TATCCTGACA TTCTCTTTAC 2110       2120       2130       2140       2150       2160
CAAATAAAAT AATTTTGTTT ATTAAAATCC CATTTTGCGA CAACTTCTTC CGCAGCTTCC 2170       2180       2190       2200       2210       2220
ATTTGCTCTT TGGTGTAATC TTCATCGCCA ACATGAACTA AATCACCATT CTCAACATCT 2230       2240       2250       2260       2270       2280
TCAAGTTTCA AATCTTGCTT AATTTGCTTT AATAATCCAC CATAGCTGAT TTGTCGTGTT 2290       2300       2310       2320       2330       2340
CCAGCTAAGG CATACTCCAA ATTTTTAATC ACCACCAAAT TACGCTCATC ATCAGCCGTC 2350       2360       2370       2380       2390       2400
ATATAATCAG CTGATTTTAC CTCGTATTTC GCCGTTTCTT CGGCACTAGC TTGCAAAGAG
```

FIG. 6B

```
      2410       2420       2430       2440       2450       2460
TCAGTTCCTT TACGTTTGTT AGCTTTAACA GCCTGCACAT GCACCACAGG CTCATAATCA 2470       2480       2490       2500       2510       2520
ACTTTCAAGG CTTTTTGCCA TAATTTTGCC CATTCTGCTT GTGCTAAATA ATTATTTGAA 2530       2540       2550       2560       2570       2580
TTCTTAAAAT AACTTGATTT TACAAACAGC AACACATGCA AGTGTTGATT ATATGACCCG 2590       2600       2610       2620       2630       2640
TCTTGTTCAT TAACGGTAAT TTCCGTTGAA CGTAAATAAC CCAATAAATT TTTAGTCACT 2650       2660       2670       2680       2690       2700
TTTTTATAGC GAGTTAGCTT ATTAAAGGCT TTAGTCAAAG CTCTTAAAGA CACTTTTAAC 2710       2720       2730       2740       2750       2760
TCCTCTGCTG AATGAGCGTT TTTAACGGTT AAAGTTAAAA ACAAAAACCG TCCTTTAGGC 2770       2780       2790       2800       2810       2820
TCTCTTGCAA CTGCTTCCGC AATAATTTGT TTTAACTGGC TCGAGTTTTT CATGCTCCTT 2830       2840       2850       2860       2870       2880
CTCCAATTAC ACAATGGACA CAATCGTTTA TGACAAAACC ACGTTTGATA AAGTTTTAAG 2890       2900       2910       2920       2930       2940
TGCTCGCCAA TCTTACGAAA ACGCAAAACT TCACCACAAC CCCGTACATC ATGTGCCCGT 2950       2960       2970       2980       2990       3000
TTAAATTCTA AGATTGCCAA ATATTCGGCA TAGCGCACAT TTTCAATCTT CCGTTCTCGC 3010       3020       3030       3040       3050       3060
CAAGGTCTAA CTTTGCCATT TTCAGTTTTA TCTTCAAAAA TTTCTGACAT AAAAAGCTCC 3070       3080       3090       3100       3110       3120
TCCAGTTTAT CCACGTGAAG GAGCTGACTA TCTTTTTCAA TAAGCTTATA ACCTTGACAT 3130       3140       3150       3160       3170       3180
CATAGGGCTT TTCCCCTAGA ATAGGCTATA AATCGCAAAT GATAATCAAC TCACGTGTTC 3190       3200       3210       3220       3230       3240
CGAGCGGCCA AACTAGGAAT TTGCACGTGG GTTTTTATTT TGTCTTTCTT TCAACCAATT 3250       3260       3270       3280       3290       3300
TATAACCCTA ATAATACACC AAAAGCCTAT AAAATCAATG GATACAAGCC CAATTAAGCC 3310       3320       3330       3340       3350       3360
TAATCAAGCT TGATTTTAAA AAACTAGTTG TTGCTAATAG TATCAAGATA AGAAGAAAAC 3370       3380       3390       3400       3410       3420
GCCAAAAATT GCGTTTTTAA ACCCCAAAAA GCAGATCAGC AAAAACCGCT GAACTGCTTT 3430       3440       3450       3460       3470       3480
TTTTAAACCG TGGCTTTCAG CCACACTGAC CAGCTGAACC AGCTGGACCG TAACGCTTGC 3490       3500       3510       3520       3530       3540
CGCCGCTGGG CTCGGGAAAA CAAGGGCTTG TTTTCCAAGA CGTCAGGCTT TTGGTATTGT 3550       3560       3570       3580       3590       3600
CTAGTCTATC AACTCCTTAA AGCCTCCAAG AGGGGCTAAT ATCGCCTGTA AGGCTCAATA
```

FIG. 6C

```
       3610       3620       3630       3640       3650       3660
AGCCCCTCTA AGTCGATTTA CCGTTGACAG ACAGTTAGAT AGCTAACTGT TAGCTAAAAT 3670       3680       3690       3700       3710       3720
CGCTTAGAAC GCAAATAAGA GCCTTTAAAA TTAACGTTCA AAAATAAAAA AGTTCGAAGG 3730       3740       3750       3760       3770       3780
AGCTAGCGAC TGAACTTATT TATTTTTGAA TGTTCCAAAC TGACGCAAGT CAGTTACGTT 3790       3800       3810       3820       3830       3840
TGAGCAACGC GAAATCTGAT GCAGGTTTTG ATGGGTTTAG CACAACACAA CTTCATGTTG 3850       3860       3870       3880       3890       3900
TGTGTAAGTG CGCACTACAT GATAATGCGC ACTACATGAT AATGCGCACT ACATGATAAT 3910       3920       3930       3940       3950       3960
GTGCGCACTA CATGATAATG CGCACTACAT GATAATGTAC ATGATAATGT GCGCACTACA 3970       3980       3990       4000       4010       4020
TGATAATGCG CACTACATGA TAATGCGCAC TACATGATAA TGCGCACTAC ATGATAATGC 4030       4040       4050       4060       4070       4080
GCACTACATG ATAATGCGCA CTACATGATA ATGCGCACTA CATGATAATG TGCACTTACA 4090       4100       4110       4120       4130       4140
CTCCAAATAA ATTGGAGTAA TGCTAAAACC TGTATCAGAA GTCAGCAAGC TGACAACAAA 4150       4160       4170       4180       4190       4200
AAAGGGATAT GCCAACGGAT TTACCGTTGA TCTCCCGATC CCCTATGGTC GACTCTCAGT 4210       4220       4230       4240       4250       4260
ACAATCTGCT CTGATGCCGC ATAGTTAAGC CAGTATCTGC TCCCTGCTTG TGTGTTGGAG 4270       4280       4290       4300       4310       4320
GTCGCTGAGT AGTGCGCGAG CAAAATTTAA GCTACAACAA GGCAAGGCTT GACCGACAAT 4330       4340       4350       4360       4370       4380
TGCATGAAGA ATCTGCTTAG GGTTAGGCGT TTTGCGCTGC TTCGTTAGAA GCAAACTAAG 4390       4400       4410       4420       4430       4440
AGTGTGTTGA GTAGTGCAGT ATCTTAAAAT TTTGTATAAT AGGAATTGAA GTTAAATTAG 4450       4460       4470       4480       4490       4500
ATGCTAAAAA TTTGTAATTA AGAAGGAGTG ATTACATGAT TGGCAGCCAG TCTCCGGGCA 4510       4520       4530       4540       4550       4560
ATTAATGAAC TTGGACATGG TTGACGACCC GGTCTTTGCA AGCCGAATTC GACCACACTG 4570       4580       4590       4600       4610       4620
GCGGCCGTTA CTAGGGTATC GATCCGATAA AAAGTTAGGC GACGGCTTTG CCCTGGTGCC 4630       4640       4650       4660       4670       4680
AGCAGACGGT AAGGTCTACG CGCCATTTGC CGGTACTGTC CGCCAGCTGG CCAAGACCCG 4690       4700       4710       4720       4730       4740
GCACTCGATC GTCCTGGAAA ATGAACATGG GGTCTTGGTC TTGATTCACC TTGGCCTGGG 4750       4760       4770       4780       4790       4800
CACGGTCAAA TTAAACGGGA CTGGCTTTGT CAGCTATGTT GAAGAGGGCA GCCAGGTAGA
```

FIG. 6D

```
      4810       4820       4830       4840       4850       4860
 AGCCGGCCAG CAGATCCTGG AATTCTGGGA CCCGGCGATC AAGCAGGCCA AGCTGGACGA 4870       4880       4890       4900       4910       4920
 CACGGTAATC GTGACCGTCA TCAACAGCGA AACTTTCACA AATAGCCAGA TGCTCTTGCC 4930       4940       4950       4960       4970       4980
 GATCGGCCAC AGCGTCCAAG CCCTGGATGA TGTATTCAAG TTAGAAGGGA AGAATTAGAA 4990       5000       5010       5020       5030       5040
 AATGAGCAAT AAGTTAGTAA AAGAAAAAAG AGTTGACCAG GCAGACCTGG CCTGGCTGAC 5050       5060       5070       5080       5090       5100
 TGACCCGGAA GTTTACGAAG TCAATACAAT TCCCCCGCAC TCCGACCATG AGTCCTTCCA 5110       5120       5130       5140       5150       5160
 AAGCCAGGAA GAACTGGAGG AGGGCAAGTC CAGTTTAGTG CAGTCCCTGG ACGGGGACTG 5170       5180       5190       5200       5210       5220
 GCTGATTGAC TACGCTGAAA ACGGCCAGGG ACCAGTCAAC TTCTATGCAG AAGACTTTGA 5230       5240       5250       5260       5270       5280
 CGATAGCAAT TTTAAGTCAG TCAAAGTACC CGGCAACCTG GAACTGCAAG GCTTTGGCCA 5290       5300       5310       5320       5330       5340
 GCCCCAGTAT GTCAACGTCC AATATCCATG GGACGGCAGT GAGGAGATTT TCCCGCCCCA 5350       5360       5370       5380       5390       5400
 AATTCCAAGC AAAAATCCGC TCGCTTCTTA TGTCAGATAC TTTGACCTGG ATGAAGCTTT 5410       5420       5430       5440       5450       5460
 CTGGGACAAG GAAGTCAGCT TGAAGTTTGA CGGGGCGGCA ACAGCCATCT ATGTCTGGCT 5470       5480       5490       5500       5510       5520
 GAACGGCCAC TTCGTCGGCT ACGGGGAAGA CTCCTTTACC CCAAGCGAGT TTATGGTTAC 5530       5540       5550       5560       5570       5580
 CAAGTTCCTC AAGAAAGAAA ATAACCGCCT GGCAGTGGCT CTCTACAAGT ATTCTTCCGC 5590       5600       5610       5620       5630       5640
 CTCCTGGCTG GAAGACCAGG ACTTCTGGCG CATGTCTGGT TTGTTCAGAT CAGTGACTCT 5650       5660       5670       5680       5690       5700
 TCAGGCCAAG CCGCGTCTGC ACTTGGAGGA CCTTAAGCTT ACGGCCAGCT TGACCGATAA 5710       5720       5730       5740       5750       5760
 CTACCAAAAA GGAAAGCTGG AAGTCGAAGC CAATATTGCC TACCGCTTGC CAAATGCCAG 5770       5780       5790       5800       5810       5820
 CTTTAAGCTG GAAGTGCGGG ATAGTGAAGG TGACTTGGTT GCTGAAAAGC TGGGCCCAAT 5830       5840       5850       5860       5870       5880
 CAGAAGCGAG CAGCTGGAAT TCACTCTGGC TGATTTGCCA GTAGCTGCCT GGAGCGCGGA 5890       5900       5910       5920       5930       5940
 AAAGCCTAAC CTTTACCAGG TCCGCCTGTA TTTATACCAG GCAGGCAGCC TCTTAGAGGT 5950       5960       5970       5980       5990       6000
 TAGCCGGCAG GAAGTGGGTT TCCGCAACTT TGAACTAAAA GACGGGATTA TGTACCTTAA
```

FIG. 6E

```
       6010       6020       6030       6040       6050       6060
CGGCCAGCGG ATCGTCTTCA AGGGGGCCAA CCGGCACGAA TTTGACAGTA AGTTGGGTCG 6070       6080       6090       6100       6110       6120
GGCTATCACG GAAGAGGATA TGATCTGGGA CATCAAGACC ATGAAGCGAA GCAACATCAA 6130       6140       6150       6160       6170       6180
TGCTGTCCGC TGCTCTCACT ACCCGAACCA GTCCCTCTTT TACCGGCTCT GTGACAAGTA 6190       6200       6210       6220       6230       6240
CGGCCTTTAC GTCATTGATG AAGCTAACCT GGAAAGCCAC GGCACCTGGG AAAAAGTGGG 6250       6260       6270       6280       6290       6300
GGGGCACGAA GATCCTAGCT TCAATGTTCC AGGCGATGAC CAGCATTGGC TGGGAGCCAG 6310       6320       6330       6340       6350       6360
CTTATCCCGG GTGAAGAACA TGATGGCTCG GACAAGAAC CATGCTTCAA TCCTAATCTG 6370       6380       6390       6400       6410       6420
GTCTTTAGGC AATGAGTCTT ACGCCGGCAC TGTCTTTGCC CAAATGGCTG ATTACGTCCG 6430       6440       6450       6460       6470       6480
GAAGGCTGAT CCGACCCGGG TTCAGCACTA TGAAGGGGTG ACCCACAACC GGAAGTTTGA 6490       6500       6510       6520       6530       6540
CGACGCCACC CAGATTGAAA GCCGGATGTA TGCTCCGGCC AAGGTAATTG AAGAATACTT 6550       6560       6570       6580       6590       6600
GACCAATAAA CCAGCCAAGC CATTTATCTC AGTTGAATAC GCTCACGCCA TGGGCAACTC 6610       6620       6630       6640       6650       6660
CGTCGGTGAC CTGGCCGCCT ACACGGCCCT GGAAAAATAC CCCCACTACC AGGGCGGCTT 6670       6680       6690       6700       6710       6720
CATCTGGGAC TGGATTGACC AAGGACTGGA AAAAGACGGG CACCTGCTTT ATGGGGGCGA 6730       6740       6750       6760       6770       6780
CTTCGATGAC CGGCCAACCG ACTATGAATT CTGCGGGAAC GGCCTGGTCT TTGCTGACCG 6790       6800       6810       6820       6830       6840
GACTGAATCG CCGAAACTGG CTAATGTCAA GGCCCTTTAC GCCAACCTTA AGTTAGAAGT 6850       6860       6870       6880       6890       6900
AAAAGATGGG CAGCTCTTCC TCAAAAACGA CAATTTATTT ACCAACAGCT CATCTTACTA 6910       6920       6930       6940       6950       6960
CTTCTTGACT AGTCTTTTGG TCGATGGCAA GTTGACCTAC CAGAGCCGGC CTCTGACCTT 6970       6980       6990       7000       7010       7020
TGGCCTGGAG CCTGGCGAAT CCGGACCTT TGCCCTGCCT TGGCCGGAAG TCGCTGATGA 7030       7040       7050       7060       7070       7080
AAAAGGGGAG GTCGTCTACC GGGTAACGGC CCACTTAAAA GAAGACTTGC CTTGGGCGGA 7090       7100       7110       7120       7130       7140
TGAGGGCTTC ACTGTGGCTG AAGCAGAAGA AGTAGCTCAA AAGCTGCCGG AATTTAAGCC 7150       7160       7170       7180       7190       7200
GGAAGGGCGG CCAGATTTAG TTGATTCCGA CTACAACCTA GGCCTGAAAG GAAATAACTT
```

FIG. 6F

```
         7210       7220       7230       7240       7250       7260
    CCAAATTCTC TTCTCCAAGG TCAAGGGCTG GCCGGTTTCC CTCAAGTATG CCGGTAGGGA 7270       7280       7290       7300       7310       7320
    ATACTTGAAG CGGCTGCCGG AATTTACCTT CTGGCGGGCC CTGACGGACA ACGACCGGGG 7330       7340       7350       7360       7370       7380
    AGCTGGTTAC GGCTATGATC TGGCCCGGTG GGAAAATGCC GGCAAGTATG CCCGCTTGAA 7390       7400       7410       7420       7430       7440
    AGACATCAGC TGCGAGGTCA AGGAAGACTC CGTTTTGGTC AAGACTGCCT TTACGTTGCC 7450       7460       7470       7480       7490       7500
    TGTCGCCTTA AAGGGTGATT TAACCGTGAC CTATGAAGTC GATGGACGGG GCAAGATTGC 7510       7520       7530       7540       7550       7560
    TGTAACAGCT GACTTCCCAG GCGCGGAAGA AGCTGGTCTC TTGCCAGCCT TTGGCTTGAA 7570       7580       7590       7600       7610       7620
    CCTGGCCCTG CCAAAAGAAC TGACCGATTA CCGCTACTAT GGTCTGGGAC CTAATGAGAG 7630       7640       7650       7660       7670       7680
    CTACCCAGAC CGCTTGGAAG GTAATTACCT GGGCATCTAC CAGGGAGCGG TAAAAAAGAA 7690       7700       7710       7720       7730       7740
    CTTTAGCCCA TATCGTCCGC AGGAAACGGG CAACCGGAGC AAGGTTCGCT GGTACCAGCT 7750       7760       7770       7780       7790       7800
    CTTTGATGAA AAGGGCGGCT TGGAATTTAC GGCCAATGGG GCAGACTTGA ACTTGTCTGC 7810       7820       7830       7840       7850       7860
    TTTGCCATAT TCTGCCGCCC AAATTGAAGC AGCGGACCAC GCTTTTGAAC TGACTAACAA 7870       7880       7890       7900       7910       7920
    TTACACTTGG GTTAGAGCCT TAAGCGCCCA GATGGGGGTC GGCGGGGATG ACTCCTGGGG 7930       7940       7950       7960       7970       7980
    GCAGAAGGTC CACCCGGAAT TCTGCCTGGA TGCTCAAAAA GCCGCCAGC TTCGCCTGGT 7990       8000       8010       8020       8030       8040
    GATTCAGCCC CTTTTACTAA AATAAATGCT ACAATTGACT TAACAGGATG AAATTTTAGT 8050       8060       8070       8080       8090       8100
    AAAAGCAAAG CGAGTGAGGA AGATGGCAAC GATCAGAGAA GTGCCAAGGC AGCCGGCGTG 8110       8120       8130       8140       8150       8160
    TCGCTAGCGA CGGTC.....  .......... .......... ..........
```

LAC SHUTTLE VECTORS

BACKGROUND OF THE INVENTION

1. Field of the Invention

The present invention relates to a Lac shuttle vector and uses thereof. More particularly, the Lac shuttle vector features a non-antibiotic resistance gene as a selection marker.

2. Description of the Related Arts

Currently, most DNA vaccines are administrated by the uptake of bacteria such as *Salmonella typhimurium* or *Listeria monocytegenes* to mammals (Dietrich G., et al., 1998, *Nature Biotech.*, 16:181–185; Lowrie, D. B., 1998, *Nature Med.*, 4:147–148). The advantage is that the DNA vaccine can be directly incorporated into immune cells, or the immune system can be stimulated by the DNA vaccine, thereby enhancing the immune response. Usually, the effect produced by the administration of such bacteria is better than that produced by using DNA alone as a vaccine. However, such kinds of attenuated bacteria may be harmful to mammals being treated or may become pathogenic due to the mutagenesis of these bacteria.

During genetic engineering, plasmids have to bear a selection marker for selection of a cell (e.g. bacteria) containing the plasmid. Generally, most commercially available plasmids bear the antibiotic resistance gene such as an ampicillin resistance gene or a kanamycin resistance gene as a selection marker. Because most of these plasmids are used in laboratories, safety is not an important concern. However, some bacteria strains present in organisms may contain the antibiotic resistance genes via the natural transduction effect. If these plasmids are used as a pharmaceutical vaccine composition or food additive, organisms treated with the plasmids or the derivatives thereof may be jeopardized. In addition, the use of antibiotics can be problematic because of the potential for residual antibiotics in the purified DNA, which can cause an allergic reaction in a treated organism.

Therefore, the object of the present invention is to construct a vector without antibiotic resistance gene and use a harmless host cell to express heterologous genes in an organism or as a DNA vaccine or health food, thereby raising the safety and enhancing the immune response.

Conventional attenuated bacteria used for DNA vaccines may cause pathogenicity. Therefore, lactic acid bacteria are selected for a vaccine medium in the present invention to achieve the above object. Lactic acid bacteria are Gram-positive bacteria without pathogenicity, and are used in large quantity in the dairy and food industries. In addition, lactic acid bacteria are normal flora present in the digestive tract (Bomba A., et al., 1994, *Vet. Med.* (praha), 39:701–710; Nemcova R., et al., 1998, *DTW Dtsch tierarztl wochenscher*, 105:199–200). Further, certain chemical composition in the cell walls of lactic acid bacteria can stimulate the immune response in human (Vilma M. A., et al., 1996, *Chem. Pharm. Bull.*, 44(12):2263–2267). If the lactic acid bacterial strains are modified so as to bear a heterologous gene or to be used as a DNA vaccine, the immunity or health of the organisms can be improved after uptake of such modified lactic acid bacteria. In addition, the recombinant plasmids or vectors can be prepared using genetic engineering to obtain more valuable lactic acid bacterial strains useful in the food industries.

SUMMARY OF THE INVENTION

In one aspect, the present invention provides a Lac shuttle vector, comprising: (a) a region which regulates a plasmid copy number, wherein said region comprises an *E. coli* replication origin sequence; (b) an eukaryotic gene expression cassette, which comprises an eukaryotic gene transcriptional promoter sequence, a multiple cloning site and a transcriptional terminator sequence, wherein a heterologous gene is inserted into said multiple cloning site; (c) a lactic acid bacteria plasmid sequence, which comprises a plus origin of replication, and a nucleic acid sequence encoding for a protein which relates to the lactic acid bacteria plasmid replication; and (d) a non-antibiotic resistance selection gene and the promoter sequence thereof.

In another aspect, the present invention provides a kit for expression of a heterologous gene, wherein the Lac shuttle vector described above incorporating the heterologous gene is introduced into a suitable system to express the heterologous protein.

In still another aspect, the present invention provides a gene vaccine carrier, in which an antigenic gene derived from pathogens or cancers is incorporated into the Lac shuttle vector described above.

In yet another aspect, the present invention provides a method for selection of a host cell containing a vector, comprising: (i) introducing into said host cell the Lac shuttle vector described above, wherein the endogenous β-galactosidase gene of said host cell is not capable of producing a normal enzymatic function; and (ii) culturing said host cell transformed in step (i) under conditions which lactose is the only carbon source.

BRIEF DESCRIPTION OF THE DRAWINGS

The present invention will be more fully understood and further advantages will become apparent when reference is made to the following description of the invention and the accompanying drawings in which:

FIG. 5(A)–(G) is a diagram showing the nucleotide sequence of the Lac shuttle vector pCLP7 (SEQ ID NO: 1).

FIG. 6(A)–(G) is a diagram showing the nucleotide sequence of the Lac shuttle vector pCLP8 (SEQ ID NO: 2).

DETAILED DESCRIPTION OF THE INVENTION

Figure 1:
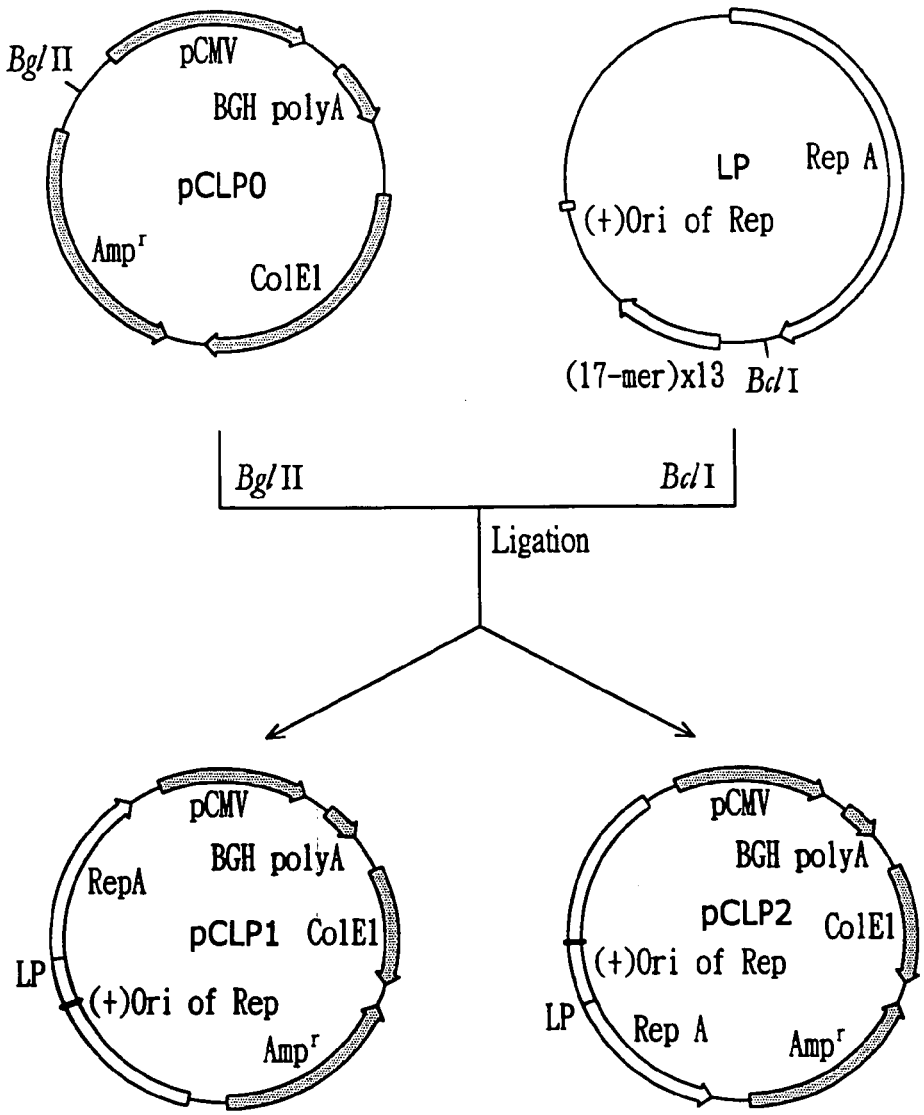
FIG. 1 is a diagram showing the constructs of the pCLP1 and pCLP2.

The term "Lac shuttle vector" used herein refers to a vector in which both plasmid replication origins of *E. coli* and *Lactobacillus* are present, so that the vector can replicate and proliferate both in *E. coli* and lactic acid bacteria, thereby breaking down the barrier between bacteria species.

For the purpose described above and for convenient manipulation subsequently, the Lac shuttle vector of the present invention comprises the replication origin, Col E1, which is necessary for the vector replication in *E. coli*.

For the purpose of expressing a heterologous protein in an eukaryotic cell or being used as a DNA vaccine carrier, the Lac shuttle vector of the present invention comprises an eukaryotic gene expression cassette, which comprises at least an eukaryotic gene transcriptional promoter sequence, a multiple cloning site and a transcriptional terminator sequence, wherein a desired heterologous gene is inserted into the multiple cloning site in the vector. Those skilled in this art will be aware that the elements that can be used in the vector described above are not limited. For example, the eukaryotic gene transcriptional promoter sequence suitable for the present invention includes cytomegalovirus (CMV) promoter, simian virus 40 (SV40) early promoter, Rous sarcoma virus (RSV) promoter, etc.

The term "vector", as used herein, refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome.

As used herein, the term "regulate", or variations such as "regulates" or "regulating", will be understood to imply sequences involved in control of a response or action. This includes sequences involved in regulating, controlling or affecting the expression of genes, or the replication, selection or maintenance of a plasmid. Examples include attenuators, operators, and promoters.

The term "replication origin" as used herein refers to a nucleotide sequence at which DNA synthesis for the purpose of replicating the nucleic acid sequence begins. This is generally termed an ori site. Bacteria generally have a single ori site, whereas there are many ori sites on each eukaryotic chromosome. This term includes replicons, which as used herein refers to a genetic element that behaves as an autonomous unit during DNA replication. In bacteria, the chromosome functions as a single replicon, whereas eukaryotic chromosomes contain hundreds of replicons in series.

The term "antibiotic resistance" as used herein refers to the acquisition of tolerance to a specific antibiotic by a microorganism that was previously adversely affected by the drug. Such resistance generally results from a mutation or the acquisition of resistance due to plasmids containing the resistance gene transforming the microorganism.

In a preferred embodiment of the present invention, the eukaryotic gene transcriptional promoter sequence is cytomegalovirus promoter (hereinafter abbreviated as "pCMV"), and transcriptional terminator sequence is bovine growth hormone polyadenylate (BGH polyA) region, which terminate and stabilize the synthesis of messenger RNA (mRNA).

There are many natural plasmids contained in Lactobacillus strains, in which the replication origins and genes encoding necessary proteins are suitable for the vector construction of the present invention. It is known that there are three different kinds of natural plasmids contained in Lactobacillus plantarum (ATCC 8014, CCRC 10357) with 2.1, 10.5, and 38.8 kb in size, respectively (Yan T-R, et at., 1996, Chinese Agri. Chem. Soc., 34:723–731). Due to the requirements of convenience and stabilization, the smallest one of the three plasmids is selected for the vector of the present invention. The plasmid of 2.1 kb in size contains a plus origin of replication, an open reading frame, and a replication control region with a sequence group of 17 nucleotides repeated 13 times; wherein the open reading frame translates a protein (Rep A protein) of 317 amino acids in length, which possesses the function associated with plasmid replication (Bouia A., et at., 1989, Plasmid, 22:185–192; Bringel F., et al., 1989, Plasmid, 22:193–202). The present invention chooses a suitable restriction enzyme such as BclI to linearize the plasmid under the condition that two important elements described above are not destroyed, so as to facilitate the linear plasmid's incorporation into the vector of the present invention.

The β-galactosidase gene in the genome of Lactobacillus delbrueckii (subsp. bulgaricus) is selected as a selection marker gene in lieu of antibiotic resistance gene. The product of β-galactosidase gene is a metabolic enzyme, which can hydrolyze lactose to glucose and galactose. (Schmidt B. F., et al., 1989, J. Bacteriol., 171:625–635). Therefore, when bacteria lack the enzyme (e.g., E. coli strain JM109) and grow under conditions which lactose is the only carbon source, the bacteria have to utilize the β-galactosidase encoded by the gene present in the plasmid to metabolize lactose to obtain the glucose required for growth (Hashiba H., 1992, Biosci. Biotech. Biochem., 56:190–194).

The β-galactosidase gene selected for the vector of the present invention is expressed under the control of a promoter. Preferably, the promoter is a strong transcriptional promoter to overexpress the gene product (Hashiba H., 1992, Biosci. Biotech. Biochem., 56:190–194). In one preferred embodiment of the present invention, the promoter is erythromycin resistance gene promoter (hereinafter abbreviated as "Em'P").

The advantages of using β-galactosidase gene as a selection marker include not only replacing antibiotic resistance gene, but also meeting the safety requirements of pharmaceuticals and foods.

In accordance with the construction of the present invention, the function of the β-galactosidase encoded by the gene of the host cell itself (i.e., endogenous β-galactosidase) has to be destroyed (i.e., the host cell can not express β-galactosidase with normal enzyme activity) so that host cell must rely on the recombinant vector of the present invention for survival. The present invention uses N-methyl-N'-nitro-N-nitrosoguanidine; MNNG) to treat the host bacteria in the log phase. MNNG is an alkylating agent, which facilitates acting on guanine and thymine to cause DNA mutation. Therefore, a bacterial strain with a defective β-galactosidase gene can be selected.

The host bacterial strain suitable for use in the present invention includes, but is not limited to Lactobacillus casei (subsp. casei). The advantages of using this strain include that: (1) this bacterial strain is one of the strains used for the production of cheese that meets the safety requirement of foods; (2) this bacterial strain can be anchored and colonized in the intestine; and (3) the shuttle vector of the present invention comprises a plus origin of replication of lactic acid bacterial plasmid, so that the vector can replicate and segregate stably in lactic acid bacterial host (Leer R., et al., 1992, Mol. Gen. Genet., 234:265–274; Posno M., et al., 1991, Appl. Environmental Microbiol. 57:1822–1828). It is to be understood that lactic acid bacterial strain is one of the Gram-positive bacteria, and the shuttle vector of the present invention bear both replication origins of E. coli and Lactobacillus. Thus, those skilled in this art will be aware that any Gram-positive bacterium with similar genetic properties to lactic acid bacteria can also be used as host cells in the present invention. That is, any appropriate bacterial strain that is mutated to possess defective β-galactosidase gene, or any appropriate bacterial strain whose endogenous β-galactosidase gene does not have normal enzyme activity, can be used in the present invention. In a preferred embodiment, *Lactobacillus casei* (subsp. *casei*) is treated with MNNG, followed by screening with X-gal and a selection medium to obtain a Lac⁻ mutant designated Ana-1. Ana-1 is deposited with American Type Culture Collection (ATCC) at 10801 University Boulevard, Manassas, Va. 20110, USA, on 10 Nov. 2000 and assigned ATCC Accession No. PTA-2662.

In the multiple cloning site of the Lac shuttle vector of the present invention, suitable antigenic genes derived from pathogens or cancers can be inserted to obtain a gene vaccine carrier. This gene vaccine carrier is then transformed into a bacterial strain with defective a β-galactosidase gene, followed by administration to organisms orally or by injection (for example, intravenously, intraarterially, subcutaneously, intraperitoneally, intracranially, or intramuscularly). Thus, the gene vaccine carrier can be incorporated into cells of organisms by endocytosis or phagocytosis. In addition, due to the construction of an eukaryotic gene transcriptional promoter sequence (e.g. pCMV), the antigenic genes in the multiple cloning site can be expressed immediately.

The use of the Lac shuttle vector in combination with the host cell with defective β-galactosidase gene as a gene vaccine has advantages as follows: (1) lactic acid bacteria is neither toxic nor pathogenic; (2) certain chemical compositions in the cell wall of lactic acid bacteria can stimulate and enhance the immune response in mammals; (3) the dosage of Lac shuttle vector used as a gene vaccine is much lower than that of the direct injection of a DNA vaccine; the former is about less than 1 mg/dose, whereas the later is about 100 mg/dose and the injection site is limited to, for example, the site near the body surface; and (4) the safety of Lac shuttle vector is much higher than the use of a viral vector.

In the multiple cloning site of the Lac shuttle vector of the present invention, a heterologous gene can also be inserted to obtain a recombinant expression vector. The heterologous protein of interested thus can be in vivo or in vitro overexpressed in a suitable eukaryotic cell by the eukaryotic gene transcriptional promoter in the vector. Those skilled in this art will be aware that the eukaryotic gene transcriptional promoter can be replaced with a suitable prokaryotic gene transcriptional promoter, so that the heterologous protein of interested can be overexpressed in an appreciate prokaryotic cell.

The transformation of vectors into a cell can be achieved via various mechanisms known to those skilled in this art. For example, transformation (including treatment with divalent cation, DMSO, reducing reagent, hexamminecobalt chloride and so on), electroporation or particle bombardment.

Without intending to limit it in any manner, the present invention will be further illustrated by the following examples.

EXAMPLE

The bacterial strains described above and used in the following examples included *Lactobacillus delbrueckii* (subsp. *bulgaricus*) (CCRC 14008), *Lactobacillus plantarum* (CCRC 10357), and *Lactobacillus casei* (subsp. *casei*) (CCRC 10697), which are available from Culture Collection and Research Center (CCRC), Hsinchu, Taiwan. All three bacteria were grown in *Lactobacilli* MRS broth (including 10 g/L proteose peptone No.3, 10 g/L beef extract, 5 g/L yeast extract, 20 g/L dextrose, 1 g/L Tween-80, 2 g/L ammonium citrate, 5 g/L $CH_3COONa$, 0.1 g/L $MgSO_4 \cdot 7H_2O$, 0.05 g/L $MnSO_4 \cdot H_2O$, 2 g/L $K_2HPO_4$, pH 6.2–6.5) at 37° C.

Example 1

Preparation of Lac⁻ Mutant Host Strain (Ana-1)

20 µl overnight culture of *Lactobacillus casei* (subsp. *casei*) was inoculated to 1 ml MRS broth and incubated at 37° C. for 4 hours. A pellet was obtained by spin-down and then washed twice with PBS buffer (50 mM potassium phosphate, 150 mM NaCl, pH 7.2). The bacterial pellet was resuspended in 0.9 ml PBS buffer and treated with 0.1 ml MNNG stock (N-methyl-N'-nitro-N-nitrosoguanidine; 5 mg/ml in 0.05 M acetic acid). After slow rotation at 37° C. for 1 hour, bacteria were pelleted down and washed three times with PBS buffer, and then resuspended in 0.1 ml MRS broth. Ten-fold serial dilution was performed with MRS broth. 0.1 ml bacteria in MRS from each dilution was spread to a diameter 100 mm agar plate, which has been spread with 40 µl of X-gal (20 mg/ml). These plates were incubated at 37° C. for 1–3 days. White colonies were selected as *Lactobacillus casei* (subsp. *casei*) Lac⁻ mutant (Ana-1).

Example 2

1. Isolation of *Lactobacillus plantarum* Plasmid

*Lactobacillus plantarum* were collected from 15 ml MRS/overnight cultured broth. The bacteria were lysed with 4.755 ml solution I (6.7% sucrose, 50 mM Tris-HCl pH 7.6, 1 mM EDTA pH 8.0, and 100 µg/ml lysozyme) at 37° C. for 20 min. After addition of 482 µl solution II (50 mM Tris-HCl pH 7.6 and 0.25 M EDTA) and 276 µl solution III (20% SDS, 50 mM Tris-HCl pH 7.6, and 20 mM EDTA), the mixture was incubated at 37° C. for 20 min and vigorously shaken for 30 sec, followed with addition of 1.276 ml of 3 N NaOH and rotation for 10 min, and addition of 496 µl of 2 M Tris and rotation for another 10 min. For extraction of bacterial protein, bacterial lysate were added with 717 µl of 5 M NaCl and 700 µl phenol saturated with 3% NaCl. After centrifugation, the aqueous phase was extracted with equal volume of chloroform-isoamylalcohol (24:1). After mixing and centrifugation, the aqueous phase was precipitated with equal volume of isopropanol at 0° C. for 1 hour and then centrifuged for 5 min to obtain DNA pellet. The DNA pellet was air dried and dissolved in 20 µl $H_2O$. The quality and quantity of the plasmid DNA was estimated by 1% agarose electrophoresis and ethidium bromide stain.

2. Cloning of *Lactobacillus plantarum* 2.1 kb Plasmid

The plasmids isolated from *Lactobacillus plantarum* were fractionated by electrophoresis on 1% agarose gel and purified by GENECLEAN III kit (Bio 101, La Jolla, Calif.). To generate plasmids pCLP1 and pCLP2, the 2.1 kb plasmid was digested with restriction enzyme BclI and ligated into the BglII site of pCLP0, which consists of CMV promoter, BGH polyA sequence, ColE1 replication origin, and $Amp^R$ open reading frame (see FIG. 1).

Example 3

1. Isolation of Chromosomal DNA from *Lactobacillus delbrueckii* (Subsp. *bulgaricus*)

*Lactobacillus delbrueckii* (subsp. *bulgaricus*) were collected from 20 ml MRS/overnight cultured broth. The bacterial pellet was resuspended in 1 ml TES buffer (100 mM Tris, 20 mM EDTA, 20% sucrose, and 1 mg/ml lysozyme) at 37° C. for 30 min. The cells were then subjected to five freeze-thaw cycles by freezing in a dry ice-ethanol bath and thawing in a 37° C. water bath. The cells were lysed by addition of ½ volume of 1% SDS (sodium dodecyl sulfate) solution. The chromosomal DNA was purified by triple phenol extractions. The DNA was finally precipitated with ethanol, air dried, and then dissolved in $H_2O$.

2. Cloning of β-galactosidase Gene

The β-galactosidase gene was amplified from chromosomal DNA of *Lactobacillus delbrueckii* (subsp. *bulgaricus*) by polymerase chain reaction (PCR). The PCR amplification consisted of 0.075 units Pfu Turbo™ DNA polymerase (STRATAGENE®, La Jolla, Calif.), 1 μM each of forward (5'-aagctcatgaTTGGCAGCCAGTCTCCGGGC-3'; SEQ ID NO:3) and reverse primers (5'-gacctcatgaAC-CGTCGCTAGCGACACGCC-3'; SEQ ID NO:4). PCR was carried out in 4 stages: (i) 95° C. for 5 min; (ii) 94° C. for 30 sec, 54° C. for 30 sec, 72° C. for 3 min, ×30 cycles; (iii) 72° C. for 10 min; and (iv) hold at 4° C. The amplified DNA product was estimated by 0.8% agarose electrophoresis and ethidium bromide stain, followed with purification by GENECLEAN III kit (Bio 101, La Jolla, Calif.). The purified 3 kb β-galactosidase DNA fragment was ligated into EcoRV site of pcDNA3 vector (INVITROGENE). The ligation mixture was transformed into *E. coli* strain DH5α. The blue-color clones containing the plasmid bearing β-galactosidase gene were selected from X-gal/Amp LB agar plate.

Example 4

Cloning of Erythromycin$^r$ Enh/promoter (Em'P) DNA Fragment and Em'P-β-galactosidase DNA Fragment The plasmid pVA838 obtained from CCRC (Hsinchu, Taiwan) was used as template for cloning of (Em'P) DNA fragment via PCR. The PCR amplification consisted of 0.075 units Pfu Turbo™ DNA polymerase (STRATAGENE®), 1 μM each of forward (5'-TTAACGATCGTTA-GAAGCAAACTTAAGAGTG-3'; SEQ ID NO:5) and reverse primers (5'-TTAACGATCGATGTAATCACTCCT-TCT-3'; SEQ ID NO:6). PCR was carried out in 4 stages: (i) 95° C. for 5 min; (ii) 94° C. for 30 sec, 50° C. for 30 sec, 72° C. for 30 sec, ×30 cycles; (iii) 72° C. for 10 min; and (iv) hold at 4° C. The amplified DNA product was estimated by 1% agarose electrophoresis and ethidium bromide stain, followed with purification by phenol/chloroform extraction and ethanol precipitation. The purified 120 bp Em'P DNA fragment was ligated into the pCRII vector (INVITROGENE). These clones bearing the pCRII/Em'P plasmid were selected from X-gal/Amp LB agar plate as white colonies and further checked by PCR and restriction enzyme analysis.

Figure 2:
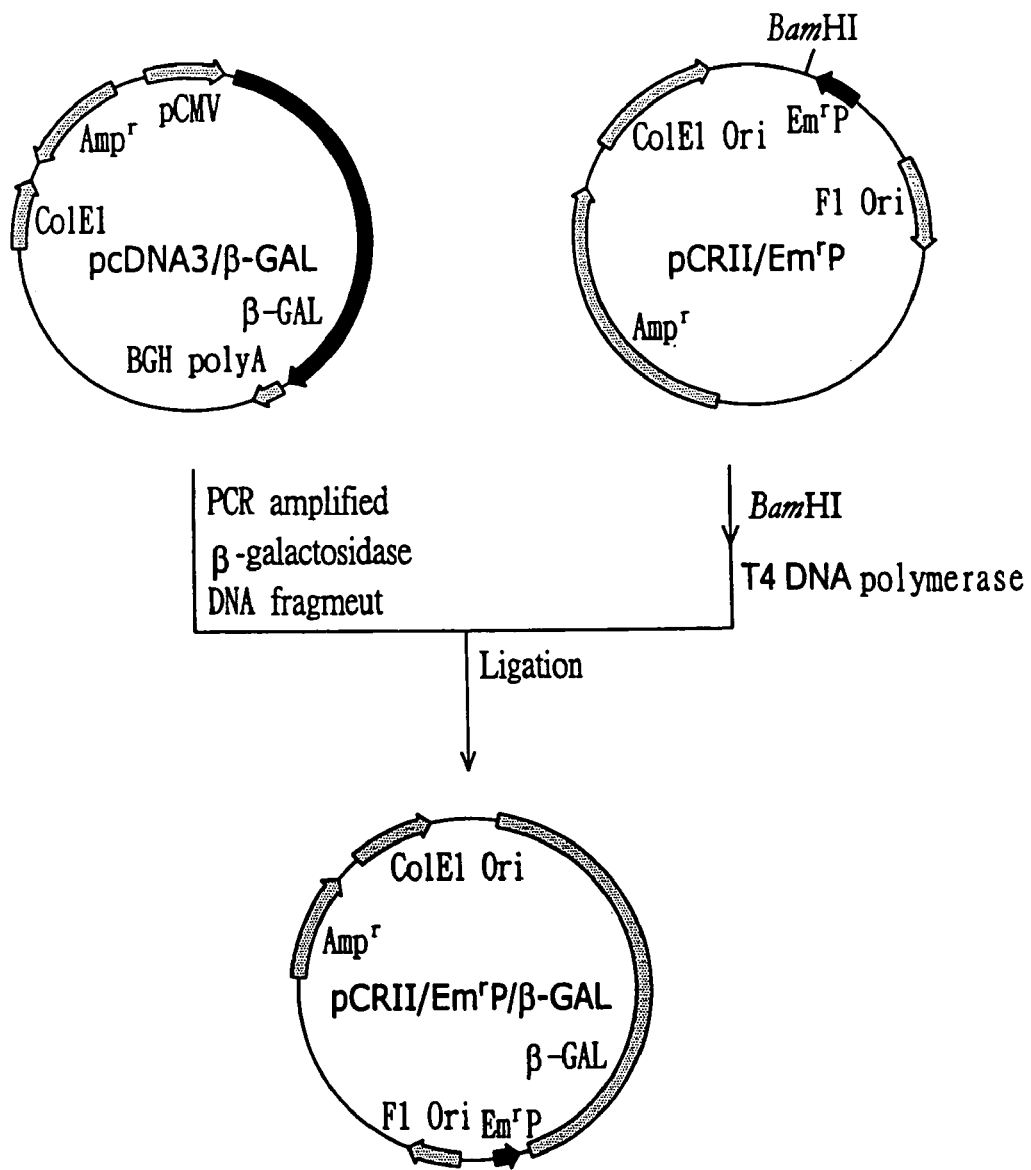
FIG. 2 is a diagram showing the construct of the pCRII/Em'P-β-galactosidase.

The pCRII/Em'P plasmid was purified by GFX Micro plasmid Prep Kit (Amersham Pharmacia Biotech.), then linearized with BamHI and blunted at the end with T4 DNA polymerase. For construction of plasmid pCRII/Em'P-β-galactosidase, the β-galactosidase DNA fragment was amplified from pcDNA3/β-galactosidase plasmid by PCR and ligated to the blunt end of linearized pCRII/Em'P. These clones bearing the pCRII/EM'P-β-galactosidase plasmid were selected from X-gal/Amp LB agar plate as blue colonies and further checked by PCR and restriction enzyme analysis (see FIG. 2).

Example 5

Cloning of Lac Shuttle Vector

Figure 3:
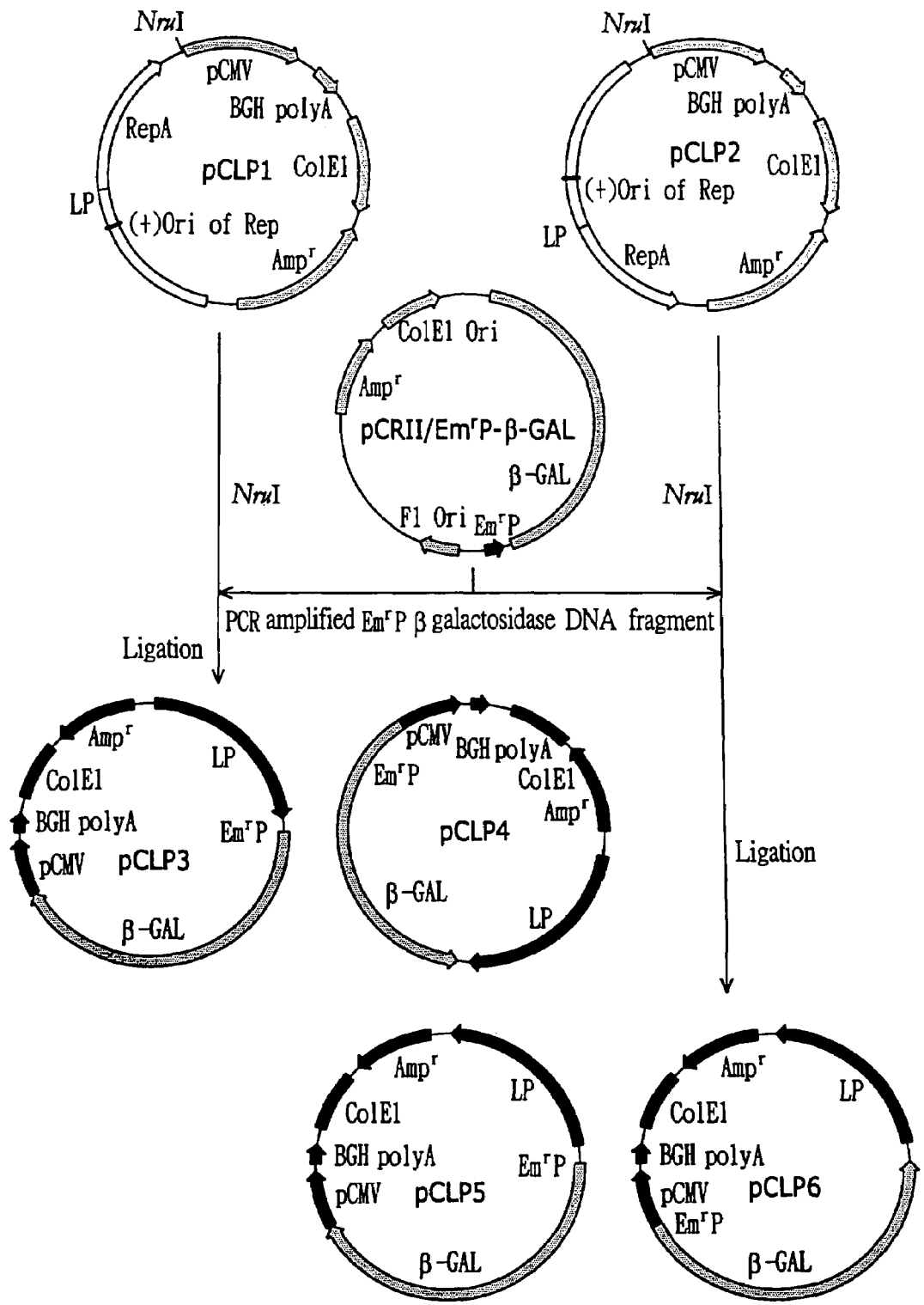
FIG. 3 is a diagram showing the constructs of the pCLP3, pCLP4, pCLP5, and pCLP6.

After phosphorylation of the 5'-end of Em'P-β-galactosidase DNA fragment amplified by PCR, the DNA fragment was purified by GENECLEAN III kit (Bio 101, La Jolla, Calif.) and ligated to the NruI site of plasmids pCLP1 and pCLP2 to obtain plasmids pCLP3–6 (see FIG. 3). The ligation mixture was electroporated to *E. coli* JM109 strain. These clones bearing the plasmid containing Em'P-β-galactosidase gene were selected from X-gal/Amp LB agar plate as blue colonies and further checked by PCR and restriction enzyme analysis.

To delete the ampicillin resistance gene from the shuttle vectors pCLP3 and pCLP5, these two plasmids were digested with BspHI. The 1 kb DNA fragment containing the ampicillin resistance gene was discarded by gel-elution of the larger DNA fragment. The purified DNA fragments were further ligated and transformed into *E. coli* JM109 strain. These clones bearing the plasmid were selected by growth on L-M9 plate (including 6 g/L $Na_2HPO_4$, 3 g/L $KH_2PO_4$, 5 g/L NaCl, 1 g/L $NH_4Cl$, 2 mM $MgSO_4$, 0.1% lactose, 0.1 mM $CaCl_2$, 2 mM proline, and 50 μM thiamine) but not on Amp/LB agar plate, and further checked by PCR and restriction enzyme analysis (see FIG. 4).

Example 6

Preparation of Ana-1 Competent Cell

To prepare the competent cell for electroporation, 1 ml overnight culture of Lac$^-$ mutant host strain from *Lactobacillus casei* (subsp. *casei*) (Example 1) was inoculated to 50 ml MRS broth supplied with 1.25% glycine and incubated at 37° C. for 3 hours. The cells were pelleted down, washed four times with ice-cold poration/storage buffer (0.5 M sucrose and 10% glycerol) and resuspended in 0.5 ml ice-cold poration/storage buffer. The plasmid DNA was purified by QIAprep Miniprer Kit (QIAGEN). 1 μg plasmid DNA was mixed with 100 μl competent cell in a disposable cuvette (STRATAGENE®; 0.2 cm interelectrode distance). A single pulse of 2500 volts (600 ohm, 25 μF) was delivered to this DNA-cell mixture. Following the pulse, the cell suspension was directly diluted with 0.4 ml MRS broth and incubated at 37° C. for 1.5 hours to allow expression of the β-galactosidase gene. The transformants were selected by plating 100 μl of the dilution of cell suspension on L-MRS agar plate, which the formula was the same as MRS, except that the dextrose was replaced with 2% lactose.

Refer to FIG. 1. Because the sequence of 5'-sticky end formed by the digestion of BclI and BglII are identical, the linear lactic acid bacteria plasmid (LP) is inserted into PCLP0 in two different directions. The resulting different plasmids are obtained by PCR amplification and restriction enzymes analysis, in which the plasmid with same direction of Rep A gene and CMV promoter is designated pCLP1, whereas the plasmid with opposite direction of Rep A gene and CMV promoter is designated pCLP2. Both pCLP1 and pCLP2 can replicate in *E. coli* for many generations and their restriction mappings can remain, indicating the copy numbers and stability of the recombinant shuttle vectors in *E. coli* are not affected after the lactic acid bacteria plasmid is inserted into the *E. coli* plasmid (pCLP0).

When the plasmids bearing β-galactosidase gene is transformed into bacteria with a defective β-galactosidase gene in the chromosome, for the purpose of survival and replication on the selective medium (with lactose but not glucose as the only carbon source), the bacteria have to overexpress the products of the selection marker gene such as β-galactosidase to metabolize the required elements. Therefore, the strong transcriptional promoter Em'P is used in the shuttle vector of the present invention. Referring to FIG. 3, after construction of Em'P-β-galactosidase, the DNA fragment is inserted into plasmids pCLP1 and pCLP2. Due to the blunt end ligation, the EM'P-β-galactosidase DNA fragment is inserted in two different directions. Four different plasmids are obtained by PCR amplification and restriction enzymes analysis, and designated pCLP3, pCLP4, pCLP5, and pCLP6, respectively. The subculture of these plasmids is then carried out for many generation, wherein the copy numbers of pCLP4 and pCLP6, and the growth of host cells transformed by these two plasmids are significantly decreased. It is thus inferred the plasmids pCLP4 and pCLP6 are structurally unstable, whereas pCLP3 and pCLP5 are relatively stable.

Figure 4:
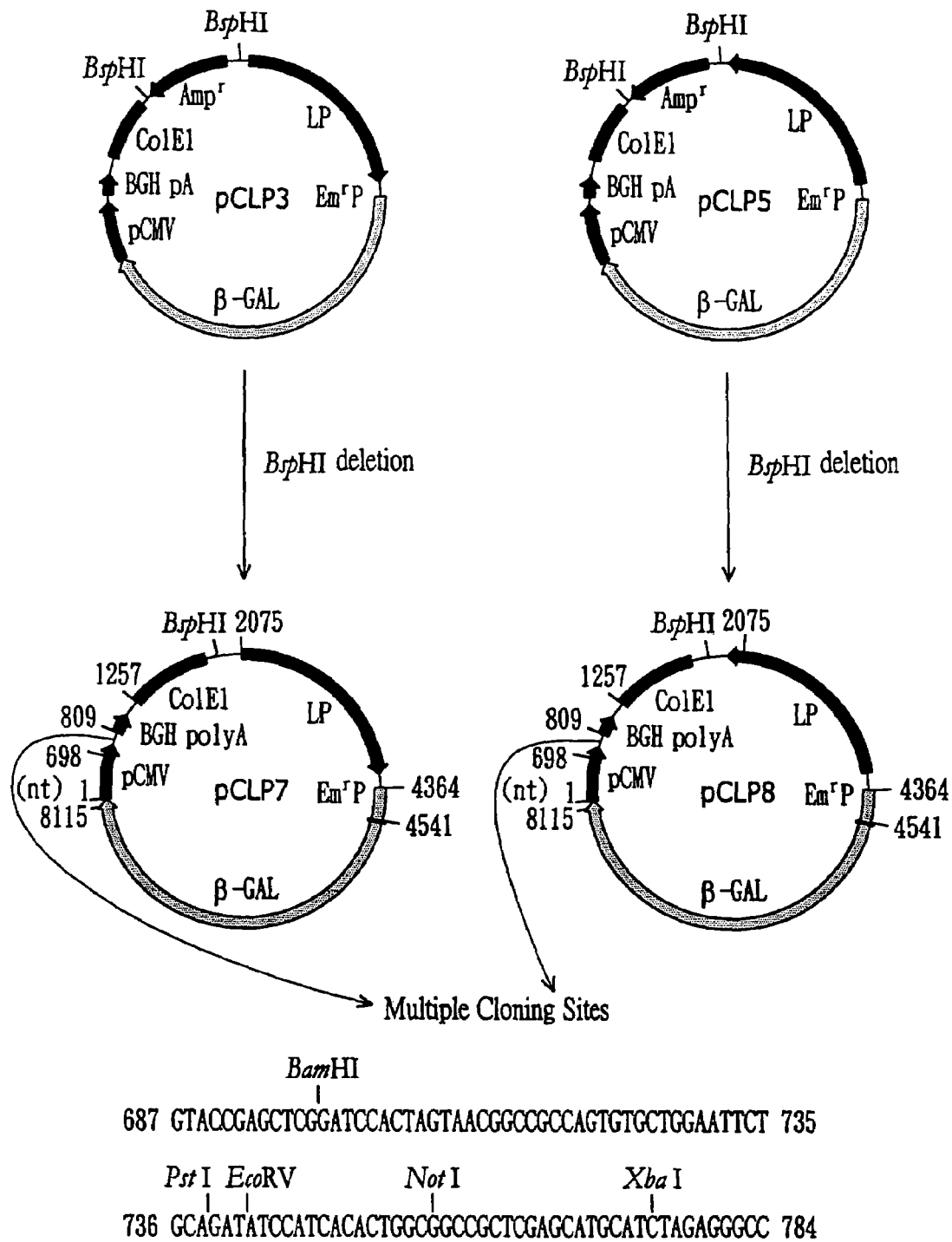
FIG. 4 is a diagram showing the constructs of the pCLP7 and pCLP8 and the sequence of the multiple cloning site comprised therein (nucleotides 687–784 of SEQ ID NO:1).
Figure 7A:
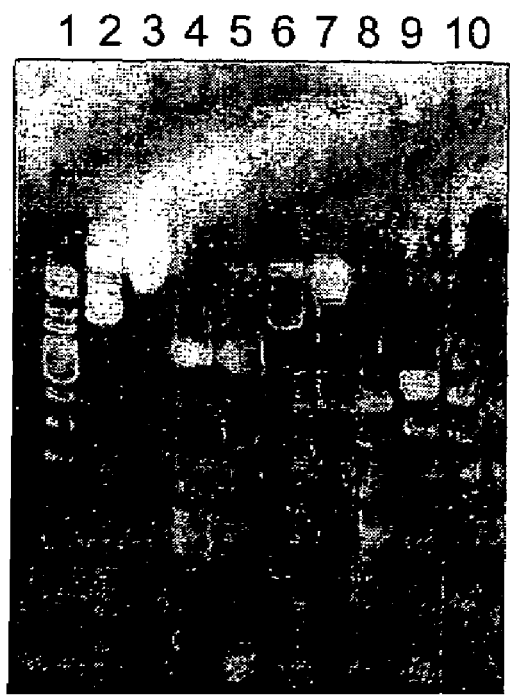
FIG. 7 is a diagram showing the stability test of vectors pCLP7 and pCLP8.

To construct the plasmid having non-antibiotic resistance gene as the selection marker, the ampicillin resistance genes of pCLP3 and pCLP5 are then deleted to obtain the plasmids pCLP7 and pCLP8 (Referring to FIG. 4). After transforming into E. coli, the bacteria can grow well in the medium which the lactose is the only carbon source. In addition, the restriction mapping analysis shows the structures of pCLP7 and pCLP8 are stable after subculture. Therefore, the stability of the shuttle vectors pCLP7 and pCLP8 makes them useful during genetic engineering. The nucleotide sequence of pCLP7 is shown in FIG. 5 (SEQ ID NO: 1) and that of pCLP8 is shown in FIG. 6 (SEQ ID NO: 2). Further, the restriction mapping of original vectors pCLP7 and pCLP8 is shown in FIG. 7A, in which lane 1 is a DNA marker (Gene Ruler™ 1 kb Ladder, MBI), lanes 2, 3 are untreated vectors, lanes 3, 7 are vectors treated with XbaI, lanes 4, 8 with EcoRI, lanes 5, 9 with HindIII, and lane 10 is another DNA marker (Gene Ruler™ 100 bp Ladder, MBI), wherein lanes 2–5 are vectors pCLP7 and lanes 6–9 are vectors pCLP8.

Figure 7B:
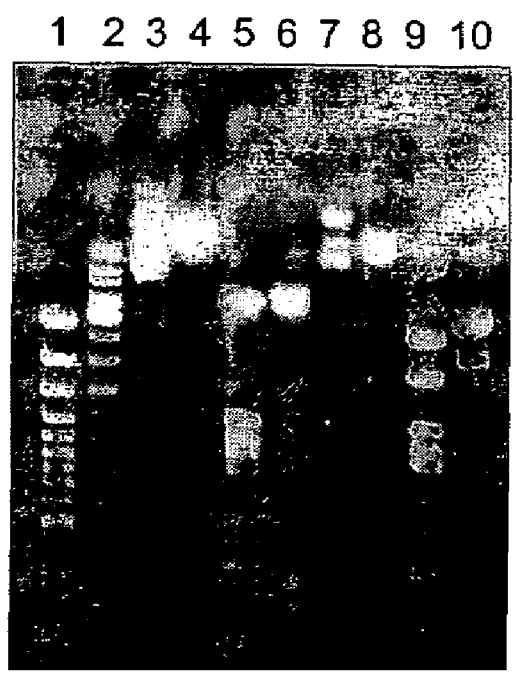

When the Lac shuttle vectors pCLP7 and pCLP8 of the present invention are transformed into Lac⁻ mutant strain Ana-1 (with defective β-galactosidase gene), the bacterial strain grows well in the selective medium. Moreover, the restriction mapping analysis also shows the structures of pCLP7 and pCLP8 are stable after 100 generations of subculture. Referring to FIG. 7B, it shows the mapping of vectors after 100 generations of subculture, in which lane 1 is a DNA marker (Gene Ruler™ 100 bp Ladder, MBI), lane 2 is another DNA marker (Gene Ruler™ 1 kb Ladder, MBI), lanes 3, 7 are untreated vectors, lanes 4, 8 are vectors treated with XbaI, lanes 5, 9 with EcoRI, and lanes 6, 10 with HindIII, wherein lanes 3–6 are vectors pCLP7 and lanes 7–10 are vectors pCLP8.

While the invention has been particularly shown and described with the reference to the preferred embodiment thereof, it will be understood by those skilled in the art that various changes in form and details may be made without departing from the spirit and scope of the invention.

What is claimed is:

1. A Lac shuttle vector, comprising:
   (a) a region which regulates a plasmid copy number, wherein said region comprises an *E. coli* replication origin sequence;
   (b) a eukaryotic gene expression cassette, which comprises a eukaryotic gene transcriptional promoter sequence, a multiple cloning site and a transcriptional terminator sequence, wherein a desired gene is inserted into said multiple cloning site;
   (c) a lactic acid bacterial plasmid sequence, which comprises a plus origin of replication, and a nucleic acid sequence encoding a Rep A protein which is involved in replication of the lactic acid bacterial plasmid; and
   (d) a marker gene that is not an antibiotic resistance gene and is operably linked to a promoter sequence.

2. The Lac shuttle vector as claimed in claim 1, wherein said eukaryotic gene transcriptional promoter is a cytomegalovirus (CMV) promoter.

3. The Lac shuttle vector as claimed in claim 1, wherein said lactic acid bacterial plasmid sequence is a plasmid of 2.1 kb in size isolated from *Lactobacillus plantarum*.

4. The Lac shuttle vector as claimed in claim 3, wherein the protein which is involved in the lactic acid bacterial plasmid replication is a Rep A protein consisting essentially of 317 amino acids.

5. The Lac shuttle vector as claimed in claim 1, wherein said marker gene is a β-galactosidase gene.

6. The Lac shuttle vector as claimed in claim 5, wherein the promoter of said β-galactosidase gene is an erythromycin resistance gene promoter.

7. The Lac shuttle vector as claimed in claim 1, wherein the Lac Shuttle vector comprises the nucleotide sequence set forth in SEQ ID NO:1 or a complementary nucleotide sequence thereto, or a degenerate variant thereof that contains degenerative protein-coding sequences.

8. The Lac shuttle vector as claimed in claim 1, wherein the Lac Shuttle vector comprises the nucleotide sequence set forth in SEQ ID NO:2 or a complementary nucleotide sequence thereto, or a degenerate variant thereof that contains degenerative protein-coding sequences.

9. The Lac shuttle vector as claimed in claim 1, wherein the Lac shuttle vector is selected from the group consisting of:
   (a) pCLP7 having the configuration of restriction sites in FIG. 4, American Type Culture Collection Accession No. PTA-2661; and
   (b) pCLP8 having the configuration of restriction sites in FIG. 4, American Type Culture Collection Accession No. PTA-2663.

10. The Lac shuttle vector as claimed in claim 1, wherein the vector is for transforming a host cell, the host cell being a Gram-positive bacterium, and the endogenous β-galactosidase gene of the host cell being non-functional.

11. The Lac shuttle vector as claimed in claim 10, wherein the host cell is the Lac- mutant of *Lactobacillus casei*, subsp. *casei*, which is designated Ana-1, American Type Culture Collection Accession No. PTA-2662.

12. A kit for expression of a gene, comprising:
   (a) the Lac shuttle vector as claimed in claim 1;
   (b) a host cell in which the endogenous β-galactosidase gene thereof is non-functional; and
   (c) a eukaryotic cell.

13. A DNA immunogenic composition comprising a Lac shuttle vector that contains:
   (a) a region which regulates a plasmid copy number, wherein said region comprises an *E. coli* replication origin sequence;
   (b) a eukaryotic gene expression cassette, which comprises a eukaryotic gene transcriptional promoter sequence, a multiple cloning site and a transcriptional terminator sequence, wherein an antigenic gene is inserted into said multiple cloning site;
   (c) a lactic acid bacterial plasmid sequence, which comprises a plus origin of replication, and a nucleic acid sequence encoding a Rep A protein which is involved in replication of the lactic acid bacterial plasmid; and
   (d) a marker gene that is not an antibiotic resistance gene and is operably linked to a promoter sequence.

14. A method for selection of a host cell containing a vector, comprising:
   (i) introducing into said host cell the Lac shuttle vector as claimed in claim 1, wherein the endogenous β-galactosidase gene of said host cell is non-functional; and
   (ii) culturing said host cell transformed in step (i) under conditions in which lactose is the only carbon source, thereby selecting a host cell comprising the Lac shuttle vector of claim 1.

* * * * *

SEQUENCE LISTING

<160> NUMBER OF SEQ ID NOS: 6

<210> SEQ ID NO 1
<211> LENGTH: 8115
<212> TYPE: DNA
<213> ORGANISM: Lactobacillus plantarum

<400> SEQUENCE: 1

```
gatgtacggg ccagatatac gcgttgacat tgattattga ctagttatta atagtaatca      60
attacggggt cattagttca tagcccatat atggagttcc gcgttacata acttacggta     120
aatggcccgc ctggctgacc gcccaacgac ccccgcccat tgacgtcaat aatgacgtat     180
gttcccatag taacgccaat agggactttc cattgacgtc aatgggtgga ctatttacgg     240
taaactgccc acttggcagt acatcaagtg tatcatatgc caagtacgcc ccctattgac     300
gtcaatgacg gtaaatggcc cgcctggcat tatgcccagt acatgacctt atgggacttt     360
cctacttggc agtacatcta cgtattagtc atcgctatta ccatggtgat gcggttttgg     420
cagtacatca atgggcgtgg atagcggttt gactcacggg gatttccaag tctccacccc     480
attgacgtca atgggagttt gttttggcac caaaatcaac gggactttcc aaaatgtcgt     540
aacaactccg ccccattgac gcaaatgggc ggtaggcgtg tacggtggga ggtctatata     600
agcagagctc tctggctaac tagagaaccc actgcttact ggcttatcga aattaatacg     660
actcactata gggagaccca agcttggtac cgagctcgga tccactagta acggccgcca     720
gtgtgctgga attctgcaga tatccatcac actggcggcc gctcgagcat gcatctagag     780
ggccctattc tatagtgtca cctaaatgct agagctcgct gatcagcctc gactgtgcct     840
tctagttgcc agccatctgt tgtttgcccc tccccgtgc cttccttgac cctggaaggt     900
```

-continued

```
gccactccca ctgtcctttc ctaataaaat gaggaaattg catcgcattg tctgagtagg      960
tgtcattcta ttctgggggg tggggtgggg caggacagca aggggagga ttgggaagac      1020
aatagcaggc atgctgggga tgcggtgggc tctatggctt ctgaggcgga aagaaccagc      1080
tgcattaatg aatcggccaa cgcgcgggga gaggcggttt gcgtattggg cgctcttccg      1140
cttcctcgct cactgactcg ctgcgctcgg tcgttcggct cgcgcagcg gtatcagctc      1200
actcaaaggc ggtaatacgg ttatccacag aatcagggga taacgcagga aagaacatgt      1260
gagcaaaagg ccagcaaaag gccaggaacc gtaaaaaggc cgcgttgctg gcgttttttcc     1320
ataggctccg cccccctgac gagcatcaca aaaatcgacg ctcaagtcag aggtggcgaa      1380
acccgacagg actataaaga taccaggcgt ttccccctgg aagctccctc gtgcgctctc      1440
ctgttccgac cctgccgctt accggatacc tgtccgcctt tctcccttcg ggaagcgtgg      1500
cgctttctca atgctcacgc tgtaggtatc tcagttcggt gtaggtcgtt cgctccaagc      1560
tgggctgtgt gcacgaaccc cccgttcagc ccgaccgctg cgccttatcc ggtaactatc      1620
gtcttgagtc caacccggta agacacgact tatcgccact ggcagcagcc actggtaaca      1680
ggattagcag agcgaggtat gtaggcggtg ctacagagtt cttgaagtgg tggcctaact      1740
acggctacac tagaaggaca gtatttggta tctgcgctct gctgaagcca gttaccttcg      1800
gaaaaagagt tggtagctct tgatccggca aacaaaccac cgctggtagc ggtggttttt      1860
ttgtttgcaa gcagcagatt acgcgcagaa aaaaaggatc tcaagaagat cctttgatct      1920
tttctacggg gtctgacgct cagtggaacg aaaactcacg ttaagggatt ttggtcatga      1980
gcggatacat atttgaatgt atttagaaaa ataaacaaat aggggttccg cgcacatttc      2040
cccgaaaagt gccacctgac gtcgacggat cgggagatca acgtaaatc cgttggcata      2100
tcccttttt gttgtcagct tgctgacttc tgatacaggt tttagcatta ctccaattta      2160
tttggagtgt aagtgcacat tatcatgtag tgcgcattat catgtagtgc gcattatcat      2220
gtagtgcgca ttatcatgta gtgcgcatta tcatgtagtg cgcattatca tgtagtgcgc      2280
attatcatgt agtgcgcaca ttatcatgta cattatcatg tagtgcgcat tatcatgtag      2340
tgcgcacatt atcatgtagt gcgcattatc atgtagtgcg cattatcatg tagtgcgcac      2400
ttacacacaa catgaagttg tgttgtgcta aacccatcaa aacctgcatc agatttcgcg      2460
ttgctcaaac gtaactgact tgcgtcagtt tggaacattc aaaaataaat aagttcagtc      2520
gctagctcct tcgaactttt ttatttttga acgttaattt taaaggctct tatttgcgtt      2580
ctaagcgatt ttagctaaca gttagctatc taactgtctg tcaacggtaa atcgacttag      2640
aggggcttat tgagccttac aggcgatatt agcccctctt ggaggcttta aggagttgat      2700
agactagaca ataccaaaag cctgacgtct tggaaaacaa gcccttgttt tcccgagccc      2760
agcggcggca agcgttacgg tccagctggt tcagctggtc agtgtggctg aaagccacgg      2820
tttaaaaaaa gcagttcagc ggttttttgct gatctgcttt tgggggttta aaaacgcaat      2880
ttttggcgtt tcttcttat cttgatacta ttagcaacaa ctagtttttt aaaatcaagc      2940
ttgattaggc ttaattgggc ttgtatccat tgattttata ggcttttggt gtattattag      3000
ggttataaat tggttgaaag aaagacaaaa taaaaaccca cgtgcaaatt cctagtttgg      3060
ccgctcggaa cacgtgagtt gattatcatt tgcgatttat agcctattct aggggaaaag      3120
ccctatgatg tcaaggttat aagcttattg aaaagatag tcagctcctt cacgtggata      3180
aactggagga gctttttatg tcagaaattt ttgaagataa aactgaaaat ggcaaagtta      3240
gaccttggcg agaacggaag attgaaaatg tgcgctatgc cgaatatttg gcaatcttag      3300
```

```
aatttaaacg ggcacatgat gtacggggtt gtggtgaagt tttgcgtttt cgtaagattg   3360
gcgagcactt aaaactttat caaacgtggt tttgtcataa acgattgtgt ccattgtgta   3420
attggagaag gagcatgaaa aactcgagcc agttaaaaca aattattgcg gaagcagttg   3480
caagagagcc taaaggacgg tttttgtttt aactttaac cgttaaaaac gctcattcag    3540
cagaggagtt aaaagtgtct ttaagagctt tgactaaagc cttaataag ctaactcgct    3600 ataaaaagt gactaaaaat ttattgggtt atttacgttc aacggaaatt accgttaatg    3660
aacaagacgg gtcatataat caacacttgc atgtgttgct gtttgtaaaa tcaagttatt   3720
ttaagaattc aaataattat ttagcacaag cagaatgggc aaaattatgg caaaaagcct   3780
tgaaagttga ttatgagcct gtggtgcatg tgcaggctgt taaagctaac aaacgtaaag   3840
gaactgactc tttgcaagct agtgccgaag aaacggcgaa atacgaggta aaatcagctg   3900
attatatgac ggctgatgat gagcgtaatt tggtggtgat taaaaatttg gagtatgcct   3960
tagctggaac acgacaaatc agctatggtg gattattaaa gcaaattaag caagatttga   4020
aacttgaaga tgttgagaat ggtgatttag ttcatgttgg cgatgaagat tacaccaaag   4080
agcaaatgga agctgcggaa gaagttgtcg caaaatggga ttttaataaa caaaattatt   4140
ttatttggta aagagaatgt caggatatga tctcccgatc ccctatggtc gactctcagt   4200
acaatctgct ctgatgccgc atagttaagc cagtatctgc tccctgcttg tgtgttggag   4260
gtcgctgagt agtgcgcgag caaaatttaa gctacaacaa ggcaaggctt gaccgacaat   4320
tgcatgaaga atctgcttag ggttaggcgt tttgcgctgc ttcgttagaa gcaaactaag   4380
agtgtgttga gtagtgcagt atcttaaaat tttgtataat aggaattgaa gttaaattag   4440
atgctaaaaa tttgtaatta agaaggagtg attacatgat tggcagccag tctccgggca   4500
attaatgaac ttggacatgg ttgacgaccc ggtctttgca agccgaattc gaccacactg   4560
gcggccgtta ctagggtatc gatccgataa aaagttaggc gacggctttg ccctggtgcc   4620
agcagacggt aaggtctacg cgccattttgc cggtactgtc cgccagctgg ccaagacccg   4680
gcactcgatc gtcctggaaa atgaacatgg ggtcttggtc ttgattcacc ttggcctggg   4740
cacggtcaaa ttaaacggga ctggctttgt cagctatgtt gaagagggca gccaggtaga   4800
agccggccag cagatcctgg aattctggga cccggcgatc aagcaggcca agctggacga   4860
cacggtaatc gtgaccgtca tcaacagcga aactttcaca aatagccaga tgctcttgcc   4920
gatcggccac agcgtccaag ccctggatga tgtattcaag ttagaaggga agaattagaa   4980
aatgagcaat aagttagtaa agaaaaaaag agttgaccag gcagacctgg cctggctgac   5040
tgacccggaa gttacgaagg tcaatacaat tcccccgcac tccgaccatg agtccttcca   5100
aagccaggaa gaactggagg agggcaagtc cagtttagtg cagtccctgg acggggactg   5160
gctgattgac tacgctgaaa acggccaggg accagtcaac ttctatgcag aagactttga   5220
cgatagcaat tttaagtcag tcaaagtacc cggcaacctg gaactgcaag gctttggcca   5280
gccccagtat gtcaacgtcc aatatccatg ggacggcagt gaggagattt ccccgcccca   5340
aattccaagc aaaaatccgc tcgcttctta tgtcagatac tttgacctgg atgaagcttt   5400
ctgggacaag gaagtcagct tgaagtttga cggggcggca acagccatct atgtctggct   5460
gaacggccac ttcgtcggct acggggaaga ctcctttacc ccaagcgagt ttatggttac   5520
caagttcctc aagaaagaaa ataaccgcct ggcagtggct ctctacaagt attcttccgc   5580
ctcctggctg aagaccagg acttctggcg catgtctggt ttgttcagat cagtgactct   5640
```

-continued

```
tcaggccaag ccgcgtctgc acttggagga ccttaagctt acggccagct tgaccgataa   5700
ctaccaaaaa ggaaagctgg aagtcgaagc caatattgcc taccgcttgc caaatgccag   5760
ctttaagctg gaagtgcggg atagtgaagg tgacttggtt gctgaaaagc tgggcccaat   5820
cagaagcgag cagctggaat tcactctggc tgatttgcca gtagctgcct ggagcgcgga   5880
aaagcctaac ctttaccagg tccgcctgta tttataccag gcaggcagcc tcttagaggt   5940
tagccggcag gaagtgggtt tccgcaactt tgaactaaaa gacgggatta tgtaccttaa   6000
cggccagcgg atcgtcttca agggggccaa ccggcacgaa tttgacagta agttgggtcg   6060
ggctatcacg gaagaggata tgatctggga catcaagacc atgaagcgaa gcaacatcaa   6120
tgctgtccgc tgctctcact acccgaacca gtccctcttt taccggctct gtgacaagta   6180
cggcctttac gtcattgatg aagctaacct ggaaagccac ggcacctggg aaaaagtggg   6240
ggggcacgaa gatcctagct tcaatgttcc aggcgatgac cagcattggc tgggagccag   6300
cttatcccgg gtgaagaaca tgatggctcg ggacaagaac catgcttcaa tcctaatctg   6360
gtctttaggc aatgagtctt acgccggcac tgtcttgcc  caaatggctg attacgtccg   6420
gaaggctgat ccgacccggg ttcagcacta tgaaggggtg acccacaacc ggaagtttga   6480
cgacgccacc cagattgaaa gccggatgta tgctccggcc aaggtaattg aagaatactt   6540
gaccaataaa ccagccaagc catttatctc agttgaatac gctcacgcca tgggcaactc   6600
cgtcggtgac ctggccgcct acacggccct ggaaaaatac ccccactacc agggcggctt   6660
catctgggac tggattgacc aaggactgga aaaagacggg cacctgcttt atgggggcga   6720
cttcgatgac cggccaaccg actatgaatt ctgcgggaac ggcctggtct ttgctgaccg   6780
gactgaatcg ccgaaactgg ctaatgtcaa ggcccttttac gccaacctta agttagaagt   6840
aaaagatggg cagctcttcc tcaaaaacga caatttattt accaacagct catcttacta   6900
cttcttgact agtctttttgg tcgatggcaa gttgacctac cagagccggc ctctgacctt   6960
tggcctggag cctggcgaat ccgggacctt tgccctgcct tggccggaag tcgctgatga   7020
aaaaggggag gtcgtctacc gggtaacggc ccacttaaaa gaagacttgc cttgggcgga   7080
tgagggcttc actgtggctg aagcagaaga agtagctcaa aagctgccgg aatttaagcc   7140
ggaagggcgg ccagatttag ttgattccga ctacaaccta ggcctgaaag gaaataactt   7200
ccaaattctc ttctccaagg tcaagggctg gccggtttcc ctcaagtatg ccggtaggga   7260
atacttgaag cggctgccgg aatttacctt ctggcgggcc ctgacggaca acgaccgggg   7320
agctggttac ggctatgatc tggcccggtg ggaaaatgcc ggcaagtatg cccgcttgaa   7380
agacatcagc tgcgaggtca aggaagactc cgttttggtc aagactgcct ttacgttgcc   7440
tgtcgcctta aagggtgatt taaccgtgac ctatgaagtc gatggacggg gcaagattgc   7500
tgtaacagct gacttcccag gcgcggaaga agctggtctc ttgccagcct ttggcttgaa   7560
cctgccctg ccaaaagaac tgaccgatta ccgctactat ggtctgggac ctaatgagag   7620
ctacccagac cgcttggaag gtaattacct gggcatctac cagggagcgg taaaaagaa   7680
ctttagccca tatcgtccgc aggaaacggg caaccgagc aaggttcgct ggtaccagct   7740
ctttgatgaa aagggcggct tggaatttac ggccaatggg gcagacttga acttgtctgc   7800
tttgccatat tctgccgccc aaattgaagc agcggaccac gcttttgaac tgactaacaa   7860
ttacacttgg gttagagcct taagcgccca gatgggggtc ggcggggatg actcctgggg   7920
gcagaaggtc caccccggaat tctgcctgga tgctcaaaaa gcccgccagc ttcgcctggt   7980
gattcagccc cttttactaa aataaatgct acaattgact taacaggatg aaattttagt   8040
```

```
aaaagcaaag cgagtgagga agatggcaac gatcagagaa gtgccaaggc agccggcgtg    8100
tcgctagcga cggtc                                                    8115

<210> SEQ ID NO 2
<211> LENGTH: 8115
<212> TYPE: DNA
<213> ORGANISM: Lactobacillus plantarum

<400> SEQUENCE: 2
gatgtacggg ccagatatac gcgttgacat tgattattga ctagttatta atagtaatca      60
attacggggt cattagttca tagcccatat atggagttcc gcgttacata acttacggta     120
aatggcccgc ctggctgacc gcccaacgac ccccgcccat tgacgtcaat aatgacgtat     180
gttcccatag taacgccaat agggactttc cattgacgtc aatgggtgga ctatttacgg     240
taaactgccc acttggcagt acatcaagtg tatcatatgc caagtacgcc ccctattgac     300
gtcaatgacg gtaaatggcc cgcctggcat tatgcccagt acatgacctt atgggacttt     360
cctacttggc agtacatcta cgtattagtc atcgctatta ccatggtgat gcggttttgg     420
cagtacatca atgggcgtgg atagcggttt gactcacggg gatttccaag tctccacccc     480
attgacgtca atgggagttt gttttggcac caaaatcaac gggactttcc aaaatgtcgt     540
aacaactccg ccccattgac gcaaatgggc ggtaggcgtg tacggtggga ggtctatata     600
agcagagctc tctggctaac tagagaaccc actgcttact ggcttatcga attaatacg      660 actcactata gggagaccca gcttggtac cgagctcgga tccactagta acggccgcca     720
gtgtgctgga attctgcaga tatccatcac actggcggcc gctcgagcat gcatctagag     780
ggccctattc tatagtgtca cctaaatgct agagctcgct gatcagcctc gactgtgcct     840
tctagttgcc agccatctgt gtttgcccc tccccgtgc cttccttgac cctggaaggt     900
gccactccca ctgtcctttc ctaataaaat gaggaaattg catcgcattg tctgagtagg     960
tgtcattcta ttctggggg tggggtgggg caggacagca agggggagga ttgggaagac    1020
aatagcaggc atgctgggga tgcggtgggc tctatggctt ctgaggcgga agaaccagc    1080 tgcattaatg aatcggccaa cgcgcgggga gaggcggttt gcgtattggg cgctcttccg    1140
cttcctcgct cactgactcg ctgcgctcgg tcgttcggct gcggcgagcg gtatcagctc    1200
actcaaaggc ggtaatacgg ttatccacag aatcagggga taacgcagga agaacatgt    1260 gagcaaaagg ccagcaaaag gccaggaacc gtaaaaaggc cgcgttgctg gcgttttttcc    1320 ataggctccg cccccctgac gagcatcaca aaaatcgacg ctcaagtcag aggtggcgaa    1380
acccgacagg actataaaga taccaggcgt ttccccctgg aagctccctc gtgcgctctc    1440
ctgttccgac cctgccgctt accggatacc tgtccgcctt tctcccttcg ggaagcgtgg    1500
cgctttctca atgctcacgc tgtaggtatc tcagttcggt gtaggtcgtt cgctccaagc    1560
tgggctgtgt gcacgaaccc cccgttcagc ccgaccgctg cgccttatcc ggtaactatc    1620
gtcttgagtc caacccggta agacacgact tatcgccact ggcagcagcc actggtaaca    1680
ggattagcag agcgaggtat gtaggcggtg ctacagagtt cttgaagtgg tggcctaact    1740
acggctacac tagaaggaca gtatttggta tctgcgctct gctgaagcca gttaccttcg    1800
gaaaaagagt tggtagctct tgatccggca aacaaaccac cgctggtagc ggtggttttt    1860
ttgtttgcaa gcagcagatt acgcgcagaa aaaaggatc tcaagaagat cctttgatct    1920
tttctacggg gtctgacgct cagtggaacg aaaactcacg ttaagggatt ttggtcatga    1980
```

```
gcggatacat atttgaatgt atttagaaaa ataaacaaat aggggttccg cgcacatttc    2040
cccgaaaagt gccacctgac gtcgacggat cgggagatca tatcctgaca ttctctttac    2100
caaataaaat aattttgttt attaaaatcc cattttgcga caacttcttc cgcagcttcc    2160
atttgctctt tggtgtaatc ttcatcgcca acatgaacta aatcaccatt ctcaacatct    2220
tcaagtttca aatcttgctt aatttgcttt aataatccac catagctgat tgtcgtgtt    2280 ccagctaagg catactccaa attttaatc accaccaaat tacgctcatc atcagccgtc    2340
atataatcag ctgattttac ctcgtatttc gccgtttctt cggcactagc ttgcaaagag    2400
tcagttcctt tacgtttgtt agcttttaaca gcctgcacat gcaccacagg ctcataatca    2460
actttcaagg cttttgcca taattttgcc cattctgctt gtgctaaata attatttgaa    2520
ttcttaaaat aacttgattt tacaaacagc aacacatgca agtgttgatt atatgacccg    2580
tcttgttcat taacggtaat ttccgttgaa cgtaaataac ccaataaatt tttagtcact    2640 ttttatagc gagttagctt attaaaggct ttagtcaaag ctcttaaaga cacttttaac    2700
tcctctgctg aatgagcgtt tttaacggtt aaagttaaaa acaaaaaccg tcctttaggc    2760
tctcttgcaa ctgcttccgc aataatttgt tttaactggc tcgagttttt catgctcctt    2820
ctccaattac acaatggaca caatcgttta tgacaaaacc acgtttgata agttttaag    2880 tgctcgccaa tcttacgaaa acgcaaaact tcaccacaac cccgtacatc atgtgcccgt    2940
ttaaattcta agattgccaa atattcggca tagcgcacat tttcaatctt ccgttctcgc    3000
caaggtctaa ctttgccatt ttcagtttta tcttcaaaaa tttctgacat aaaaagctcc    3060
tccagtttat ccacgtgaag gagctgacta tcttttttcaa taagcttata accttgacat    3120
catagggctt tccccctaga ataggctata aatcgcaaat gataatcaac tcacgtgttc    3180
cgagcggcca aactaggaat ttgcacgtgg gttttatttt tgtctttctt tcaaccaatt    3240 tataaccctra ataatacacc aaaagcctat aaaatcaatg gatacaagcc caattaagcc    3300
taatcaagct tgattttaaa aaactagttg ttgctaatag tatcaagata agaagaaaac    3360
gccaaaaatt gcgttttttaa accccaaaaa gcagatcagc aaaaaccgct gaactgcttt    3420
ttttaaaccg tggctttcag ccacactgac cagctgaacc agctggaccg taacgcttgc    3480
cgccgctggg ctcgggaaaa caagggcttg ttttccaaga cgtcaggctt ttggtattgt    3540
ctagtctatc aactccttaa agcctccaag aggggctaat atcgcctgta aggctcaata    3600
agcccctcta agtcgattta ccgttgacag acagttagat agctaactgt tagctaaaat    3660
cgcttagaac gcaaataaga gcctttaaaa ttaacgttca aaaataaaaa agttcgaagg    3720
agctagcgac tgaacttatt tattttttgaa tgttccaaac tgacgcaagt cagttacgtt    3780
tgagcaacgc gaaatctgat gcaggttttg atgggtttag cacaacacaa cttcatgttg    3840
tgtgtaagtg cgcactacat gataatgcgc actacatgat aatgcgcact acatgataat    3900
gtgcgcacta catgataatg cgcactacat gataatgtac atgataatgt gcgcactaca    3960
tgataatgcg cactcatga taatgcgcac tacatgataa tgcgcactac atgataatgc    4020
gcactacatg ataatgcgca ctacatgata atgcgcacta catgataatg tgcacttaca    4080
ctccaaataa attggagtaa tgctaaaacc tgtatcagaa gtcagcaagc tgacaacaaa    4140
aaagggatat gccaacggat ttaccgttga tctcccgatc ccctatggtc gactctcagt    4200
acaatctgct ctgatgccgc atagttaagc cagtatctgc tccctgcttg tgtgttggag    4260
gtcgctgagt agtgcgcgag caaaatttaa gctacaacaa ggcaaggctt gaccgacaat    4320
tgcatgaaga atctgcttag ggttaggcgt tttgcgctgc ttcgttagaa gcaaactaag    4380
```

-continued

```
agtgtgttga gtagtgcagt atcttaaaat tttgtataat aggaattgaa gttaaattag   4440
atgctaaaaa tttgtaatta agaaggagtg attacatgat tggcagccag tctccgggca   4500
attaatgaac ttggacatgg ttgacgaccc ggtctttgca agccgaattc gaccacactg   4560
gcggccgtta ctagggtatc gatccgataa aaagttaggc gacggctttg ccctggtgcc   4620
agcagacggt aaggtctacg cgccatttgc cggtactgtc cgccagctgg ccaagacccg   4680
gcactcgatc gtcctggaaa atgaacatgg ggtcttggtc ttgattcacc ttggcctggg   4740
cacggtcaaa ttaaacggga ctggctttgt cagctatgtt gaagagggca gccaggtaga   4800
agccggccag cagatcctgg aattctggga cccggcgatc aagcaggcca agctggacga   4860
cacggtaatc gtgaccgtca tcaacagcga aactttcaca aatagccaga tgctcttgcc   4920
gatcggccac agcgtccaag ccctggatga tgtattcaag ttagaaggga agaattagaa   4980
aatgagcaat aagttagtaa agaaaaaaag agttgaccag gcagacctgg cctggctgac   5040
tgacccggaa gtttacgaag tcaatacaat tcccccgcac tccgaccatg agtccttcca   5100
aagccaggaa gaactggagg agggcaagtc cagtttagtg cagtccctgg acggggactg   5160
gctgattgac tacgctgaaa acggccaggg accagtcaac ttctatgcag aagactttga   5220
cgatagcaat tttaagtcag tcaaagtacc cggcaacctg gaactgcaag gctttggcca   5280
gccccagtat gtcaacgtcc aatatccatg ggacggcagt gaggagattt cccgcccca    5340
aattccaagc aaaatccgc tcgcttctta tgtcagatac tttgacctgg atgaagcttt    5400
ctgggacaag gaagtcagct tgaagtttga cggggcggca acagccatct atgtctggct   5460
gaacggccac ttcgtcggct acggggaaga ctccttttacc ccaagcgagt ttatggttac  5520
caagttcctc aagaaagaaa ataaccgcct ggcagtggcc tctacaagt attcttccgc    5580
ctcctggctg aagaccagg acttctggcg catgtctggt ttgttcagat cagtgactct    5640
tcaggccaag ccgcgtctgc acttggagga ccttaagctt acggccagct tgaccgataa   5700
ctaccaaaaa ggaaagctgg aagtcgaagc caatattgcc taccgcttgc caaatgccag   5760
ctttaagctg gaagtgcggg atagtgaagg tgacttggtt gctgaaaagc tgggcccaat   5820
cagaagcgag cagctggaat tcactctggc tgatttgcca gtagctgcct ggagcgcgga   5880
aaagcctaac ctttaccagg tccgcctgta tttataccag gcaggcagcc tcttagaggt   5940
tagccggcag gaagtgggtt tccgcaactt tgaactaaaa gacgggatta tgtaccttaa   6000
cggccagcgg atcgtcttca aggggccaa ccggcacgaa tttgacagta agttgggtcg    6060
ggctatcacg gaagaggata tgatctggga catcaagacc atgaagcgaa gcaacatcaa   6120
tgctgtccgc tgctctcact acccgaacca gtccctcttt taccggctct gtgacaagta   6180
cggcctttac gtcattgatg aagctaacct ggaaagccac ggcacctggg aaaaagtggg   6240
ggggcacgaa gatcctagct tcaatgttcc aggcgatgac cagcattggc tgggagccag   6300
cttatcccgg gtgaagaaca tgatggctcg ggacaagaac catgcttcaa tcctaatctg   6360
gtctttaggc aatgagtctt acgccggcac tgtctttgcc caaatggctg attacgtccg   6420
gaaggctgat ccgacccggg ttcagcacta tgaagggtg acccacaacc ggaagtttga   6480
cgacgccacc cagattgaaa gccggatgta tgctccggcc aagtaattg aagaatactt    6540
gaccaataaa ccagccaagc catttatctc agttgaatac gctcacgcca tgggcaactc   6600
cgtcggtgac ctggccgcct acacggccct ggaaaaatac ccccactacc agggcgcctt   6660
catctgggac tggattgacc aaggactgga aaaagacggg cacctgcttt atgggggcga   6720
```

-continued

```
cttcgatgac cggccaaccg actatgaatt ctgcgggaac ggcctggtct tgctgaccg     6780 gactgaatcg ccgaaactgg ctaatgtcaa ggcccttta gccaacctta agttagaagt      6840
aaaagatggg cagctcttcc tcaaaaacga caatttattt accaacagct catcttacta    6900
cttcttgact agtcttttgg tcgatggcaa gttgacctac cagagccggc ctctgacctt    6960
tggcctggag cctggcgaat ccgggacctt tgccctgcct tggccggaag tcgctgatga    7020 aaaagggag gtcgtctacc gggtaacggc ccacttaaaa gaagacttgc cttgggcgga    7080
tgagggcttc actgtggctg aagcagaaga agtagctcaa aagctgccgg aatttaagcc    7140
ggaagggcgg ccagatttag ttgattccga ctacaaccta ggcctgaaag gaataactt    7200 ccaaattctc ttctccaagg tcaagggctg gccggtttcc ctcaagtatg ccggtaggga    7260
atacttgaag cggctgccgg aatttacctt ctggcgggcc ctgacggaca acgaccgggg    7320
agctggttac ggctatgatc tggcccggtg ggaaaatgcc ggcaagtatg cccgcttgaa    7380
agacatcagc tgcgaggtca aggaagactc cgttttggtc aagactgcct ttacgttgcc    7440 tgtcgccta aagggtgatt taaccgtgac ctatgaagtc gatggacggg gcaagattgc    7500
tgtaacagct gacttcccag gcgcggaaga agctggtctc ttgccagcct ttggcttgaa    7560
cctggccctg ccaaaagaac tgaccgatta ccgctactat ggtctgggac ctaatgagag    7620
ctacccagac cgcttggaag gtaattacct gggcatctac cagggagcgg taaaaaagaa    7680
ctttagccca tatcgtccgc aggaaacggg caaccggagc aaggttcgct ggtaccagct    7740 cttgatgaa aagggcggct tggaatttac ggccaatggg gcagacttga acttgtctgc    7800
tttgccatat tctgccgccc aaattgaagc agcggaccac gcttttgaac tgactaacaa    7860
ttacacttgg gttagagcct taagcgccca gatgggggtc ggcggggatg actcctgggg    7920
gcagaaggtc cacccggaat tctgcctgga tgctcaaaaa gcccgccagc ttcgcctggt    7980
gattcagccc cttttactaa aataaatgct acaattgact taacaggatg aaattttagt    8040
aaaagcaaag cgagtgagga agatggcaac gatcagagaa gtgccaaggc agccggcgtg    8100
tcgctagcga cggtc                                                     8115
```

<210> SEQ ID NO 3
<211> LENGTH: 30
<212> TYPE: DNA
<213> ORGANISM: Artificial Sequence
<220> FEATURE:
<223> OTHER INFORMATION: oligonucleotide for PCR

<400> SEQUENCE: 3
aagctcatga ttggcagcca gtctccgggc     30

<210> SEQ ID NO 4
<211> LENGTH: 30
<212> TYPE: DNA
<213> ORGANISM: Artificial Sequence
<220> FEATURE:
<223> OTHER INFORMATION: oligonucleotide for PCR

<400> SEQUENCE: 4
gacctcatga accgtcgcta gcgacacgcc     30

<210> SEQ ID NO 5
<211> LENGTH: 31
<212> TYPE: DNA
<213> ORGANISM: Artificial Sequence
<220> FEATURE:
<223> OTHER INFORMATION: oligonucleotide for PCR -continued

```
<400> SEQUENCE: 5
ttaacgatcg ttagaagcaa acttaagagt g                                    31

<210> SEQ ID NO 6
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 6
ttaacgatcg atgtaatcac tccttct                                         27
```